(12) United States Patent
McGinley et al.

(10) Patent No.: US 10,478,219 B2
(45) Date of Patent: Nov. 19, 2019

(54) SURGICAL ACCESS PORT

(71) Applicant: APPLIED MEDICAL RESOURCES CORPORATION, Rancho Santa Margarita, CA (US)

(72) Inventors: Kimball B. McGinley, Rancho Santa Margarita, CA (US); Henry Kahle, Corona, CA (US); Scott V. Taylor, Rancho Santa Margarita, CA (US); Gary M. Johnson, Rancho Santa Margarita, CA (US)

(73) Assignee: Applied Medical Resources Corporation, Rancho Santa Margarita, CA (US)

(*) Notice: Subject to any disclaimer, the term of this patent is extended or adjusted under 35 U.S.C. 154(b) by 78 days.

(21) Appl. No.: 15/802,213

(22) Filed: Nov. 2, 2017

(65) Prior Publication Data

US 2018/0116692 A1    May 3, 2018

Related U.S. Application Data

(63) Continuation of application No. 14/636,252, filed on Mar. 3, 2015, now Pat. No. 9,833,259, which is a
(Continued)

(51) Int. Cl.
*A61B 17/34* (2006.01)
*A61M 13/00* (2006.01)
(Continued)

(52) U.S. Cl.
CPC ...... *A61B 17/3423* (2013.01); *A61B 17/0218* (2013.01); *A61B 17/3462* (2013.01);
(Continued)

(58) Field of Classification Search
CPC ............ A61B 17/0218; A61B 17/3417; A61B 17/3423; A61B 17/3462; A61B 17/3474;
(Continued)

(56) References Cited

U.S. PATENT DOCUMENTS 3,100,482 A    8/1963 Hett
3,542,380 A    11/1970 Klein et al.
(Continued)

FOREIGN PATENT DOCUMENTS

EP    1 520 540 A1    4/2005
WO    WO 94/19052    9/1994
(Continued)

OTHER PUBLICATIONS

European Patent Office, International Search Report and the Written Opinion for International Application No. PCT/US2006/060019, dated May 14, 2005.
(Continued)

*Primary Examiner* — Brandy S Lee
(74) *Attorney, Agent, or Firm* — John F. Heal

(57) ABSTRACT

A surgical access port or trocar is provided. The trocar has a trocar seal housing and a trocar cannula with an optical obturator insertable through the trocar seal housing and the trocar cannula. The trocar is configured to access a body cavity, to maintain positive pressure and to prevent loss of surgical insufflation gas used in laparoscopic procedures. The trocar seal housing can be releasably attached to the trocar cannula. The trocar seal housing may also have a shield and/or alignment channel that provide protection or assist in operation of instrument and zero seals housed in the trocar seal housing.

18 Claims, 40 Drawing Sheets

Related U.S. Application Data continuation of application No. 13/872,340, filed on Apr. 29, 2013, now Pat. No. 8,968,250, which is a continuation of application No. 11/549,926, filed on Oct. 16, 2006, now Pat. No. 8,430,851.

(60) Provisional application No. 60/726,825, filed on Oct. 14, 2005, provisional application No. 60/828,515, filed on Oct. 6, 2006.

(51) Int. Cl.
  *A61B 17/02* (2006.01)
  *A61B 17/00* (2006.01)
  *A61M 39/22* (2006.01)

(52) U.S. Cl.
  CPC ....... *A61M 13/003* (2013.01); *A61B 17/3417* (2013.01); *A61B 17/3474* (2013.01); *A61B 2017/0046* (2013.01); *A61B 2017/00477* (2013.01); *A61B 2017/347* (2013.01); *A61B 2017/3419* (2013.01); *A61B 2017/3464* (2013.01); *A61M 39/223* (2013.01); *A61M 2039/229* (2013.01)

(58) Field of Classification Search
  CPC .. A61B 2017/0046; A61B 2017/00477; A61B 2017/3419; A61B 2017/3464; A61B 2017/347; A61M 13/003; A61M 2039/229; A61M 39/223
  See application file for complete search history.

(56) References Cited

U.S. PATENT DOCUMENTS

| | | |
|---|---|---|
| 3,613,684 A | 10/1971 | Sheridan |
| 4,147,184 A | 4/1979 | Jess |
| 4,180,542 A | 12/1979 | Wrasman |
| 4,576,589 A | 3/1986 | Kraus et al. |
| 4,655,752 A | 4/1987 | Honkanen et al. |
| 5,043,126 A | 8/1991 | Thurau |
| 5,053,016 A | 10/1991 | Lander |
| 5,112,308 A | 5/1992 | Olsen et al. |
| 5,116,353 A | 5/1992 | Green |
| 5,186,712 A | 2/1993 | Kelso et al. |
| 5,197,955 A | 3/1993 | Stephens et al. |
| 5,209,737 A | 5/1993 | Ritchart et al. |
| 5,211,370 A | 5/1993 | Powers |
| 5,224,930 A | 7/1993 | Spaeth et al. |
| 5,226,891 A | 7/1993 | Bushatz et al. |
| 5,242,412 A | 9/1993 | Blake, III |
| 5,261,888 A | 11/1993 | Semm |
| 5,273,545 A | 12/1993 | Hunt et al. |
| 5,290,245 A | 3/1994 | Dennis |
| 5,295,993 A | 3/1994 | Green |
| 5,300,035 A | 4/1994 | Clement |
| 5,300,036 A | 4/1994 | Mueller et al. |
| 5,308,336 A | 5/1994 | Hart et al. |
| 5,312,362 A | 5/1994 | Pfolsgraf et al. |
| 5,312,363 A | 5/1994 | Ryan et al. |
| 5,330,497 A | 7/1994 | Freitas et al. |
| 5,334,150 A | 8/1994 | Kaali |
| 5,342,315 A | 8/1994 | Rowe et al. |
| 5,354,280 A | 10/1994 | Haber et al. |
| 5,356,421 A | 10/1994 | Castro |
| 5,360,417 A | 11/1994 | Gravener et al. |
| 5,372,588 A | 12/1994 | Farley et al. |
| 5,385,552 A | 1/1995 | Haber et al. |
| 5,385,553 A | 1/1995 | Hart et al. |
| 5,385,572 A | 1/1995 | Nobles et al. |
| 5,391,153 A | 2/1995 | Haber et al. |
| 5,407,433 A | 4/1995 | Loomas |
| 5,411,483 A | 5/1995 | Loomas et al. |
| 5,423,761 A | 6/1995 | Hein et al. |
| 5,431,151 A | 7/1995 | Riek et al. |
| 5,445,142 A | 8/1995 | Hassler, Jr. |
| 5,454,791 A | 10/1995 | Tovey et al. |
| 5,456,673 A | 10/1995 | Ziegler et al. |
| 5,458,608 A | 10/1995 | Wortrich |
| 5,458,640 A | 10/1995 | Gerrone |
| 5,472,216 A | 12/1995 | Albertson et al. |
| 5,476,475 A | 12/1995 | Gadberry |
| 5,492,304 A | 2/1996 | Smith et al. |
| 5,496,280 A | 3/1996 | Vandenbroek et al. |
| 5,538,509 A | 7/1996 | Dunlap et al. |
| 5,545,142 A | 8/1996 | Stephens et al. |
| 5,545,150 A | 8/1996 | Danks et al. |
| 5,549,583 A | 8/1996 | Sanford et al. |
| 5,554,124 A | 9/1996 | Alvarado |
| 5,578,016 A | 11/1996 | Zinger |
| 5,584,850 A | 12/1996 | Hart et al. |
| 5,591,192 A | 1/1997 | Privitera et al. |
| 5,603,702 A | 2/1997 | Smith et al. |
| 5,607,440 A | 3/1997 | Danks et al. |
| 5,616,131 A | 4/1997 | Sauer et al. |
| 5,618,309 A | 4/1997 | Green et al. |
| 5,628,732 A | 5/1997 | Antoon, Jr. et al. |
| 5,643,301 A | 7/1997 | Mollenauer |
| 5,653,718 A | 8/1997 | Yoon |
| 5,657,963 A | 8/1997 | Hinchiffe et al. |
| 5,658,306 A | 8/1997 | Kieturakis et al. |
| 5,662,615 A | 9/1997 | Blake, III |
| 5,685,820 A | 11/1997 | Riek et al. |
| 5,690,664 A | 11/1997 | Sauer et al. |
| 5,709,664 A | 1/1998 | Vandenbroek et al. |
| 5,720,759 A | 2/1998 | Green et al. |
| 5,722,958 A | 3/1998 | Gravener et al. |
| 5,727,770 A | 3/1998 | Dennis |
| 5,738,628 A | 4/1998 | Sierocuk et al. |
| 5,792,113 A | 8/1998 | Kramer et al. |
| 5,797,944 A | 8/1998 | Obles et al. |
| 5,807,338 A | 9/1998 | Smith et al. |
| 5,817,061 A | 10/1998 | Goodwin et al. |
| 5,820,604 A | 10/1998 | Fox et al. |
| 5,820,606 A | 10/1998 | Davis et al. |
| 5,827,228 A | 10/1998 | Rowe |
| 5,855,566 A | 1/1999 | Dunlap et al. |
| 5,860,996 A | 1/1999 | Urban et al. |
| 5,865,812 A | 2/1999 | Correia |
| 5,871,471 A | 2/1999 | Ryan et al. |
| 5,871,473 A | 2/1999 | Strauss et al. |
| 5,895,377 A | 4/1999 | Smith et al. |
| 5,928,208 A | 7/1999 | Chu et al. |
| 5,941,852 A | 8/1999 | Dunlap et al. |
| 5,989,224 A | 11/1999 | Exline et al. |
| 5,989,228 A | 11/1999 | Danks et al. |
| 6,003,553 A | 12/1999 | Wahlberg |
| 6,004,326 A | 12/1999 | Castro et al. |
| 6,017,356 A | 1/2000 | Frederick et al. |
| 6,036,711 A | 3/2000 | Mozdzierz et al. |
| RE36,702 E | 5/2000 | Green et al. |
| 6,066,117 A | 5/2000 | Fox et al. |
| 6,083,203 A | 7/2000 | Yoon |
| 6,099,505 A | 8/2000 | Ryan et al. |
| 6,123,689 A | 9/2000 | To et al. |
| 6,196,967 B1 | 3/2001 | Lim et al. |
| 6,197,002 B1 | 3/2001 | Peterson |
| 6,203,557 B1 | 3/2001 | Chin |
| 6,206,875 B1 | 3/2001 | Long et al. |
| 6,228,061 B1 | 5/2001 | Flatland et al. |
| 6,258,065 B1 | 7/2001 | Dennis et al. |
| 6,270,454 B1 | 8/2001 | Sano et al. |
| 6,340,358 B1 | 1/2002 | Bohannon et al. |
| 6,423,036 B1 | 7/2002 | Van Huizen |
| 6,482,181 B1 | 11/2002 | Racenet et al. |
| 6,497,716 B1 | 12/2002 | Green et al. |
| 6,569,119 B1 | 5/2003 | Haberland et al. |
| 6,569,120 B1 | 5/2003 | Green et al. |
| 6,589,212 B1 | 7/2003 | Navis |
| 6,595,946 B1 | 7/2003 | Pasqualucci |
| 6,656,198 B2 | 12/2003 | Tsonton et al. |
| 6,685,630 B2 | 2/2004 | Sauer et al. |
| 6,695,815 B2 | 2/2004 | Moenning |
| 6,695,816 B2 | 2/2004 | Cassidy, Jr. |

(56) References Cited

U.S. PATENT DOCUMENTS

| | | |
|---|---|---|
| 6,702,787 B2 | 3/2004 | Racenet et al. |
| 6,726,663 B1 | 4/2004 | Dennis |
| 6,811,546 B1 | 11/2004 | Callas et al. |
| 6,860,869 B2 | 3/2005 | Dennis |
| 6,923,783 B2 | 8/2005 | Pasqualucci |
| 6,938,902 B2 | 9/2005 | Devers |
| 6,942,671 B1 | 9/2005 | Smith |
| 6,981,966 B2 | 1/2006 | Green et al. |
| 7,056,303 B2 | 6/2006 | Dennis et al. |
| 7,083,626 B2 | 8/2006 | Hart et al. |
| 7,390,317 B2 | 6/2008 | Taylor et al. |
| 7,717,878 B2 | 5/2010 | Smith |
| 7,984,730 B2 | 7/2011 | Ziv et al. |
| 2002/0010424 A1 | 1/2002 | Dennis et al. |
| 2003/0004529 A1 | 1/2003 | Tsonton et al. |
| 2003/0040711 A1 | 2/2003 | Racenet et al. |
| 2003/0060770 A1 | 3/2003 | Wing et al. |
| 2003/0066978 A1 | 4/2003 | Enerson |
| 2004/0068232 A1 | 4/2004 | Hart et al. |
| 2004/0106942 A1 | 6/2004 | Taylor |
| 2004/0147809 A1 | 7/2004 | Kazakevich |
| 2004/0158126 A1 | 8/2004 | Sauer et al. |
| 2004/0167473 A1 | 8/2004 | Moenning |
| 2004/0171990 A1 | 9/2004 | Dennis et al. |
| 2004/0204682 A1 | 10/2004 | Smith |
| 2004/0210162 A1 | 10/2004 | Wyatt et al. |
| 2004/0230161 A1 | 11/2004 | Zeiner |
| 2004/0260244 A1 | 12/2004 | Piechowicz et al. |
| 2005/0033342 A1 | 2/2005 | Hart et al. |
| 2005/0065475 A1 | 3/2005 | Hart et al. |
| 2005/0065543 A1 | 3/2005 | Kahle et al. |
| 2005/0070850 A1 | 3/2005 | Albrecht |
| 2005/0070851 A1 | 3/2005 | Thompson et al. |
| 2005/0070947 A1* | 3/2005 | Franer ............... A61B 17/3462 606/185 |
| 2005/0131349 A1 | 6/2005 | Albrecht et al. |
| 2005/0209608 A1 | 9/2005 | O'Heeron |
| 2005/0212221 A1 | 9/2005 | Smith et al. |
| 2005/0251191 A1 | 11/2005 | Taylor et al. |
| 2008/0077169 A1 | 3/2008 | Taylor et al. |
| 2011/0233435 A1 | 9/2011 | Matsumoto et al. |

FOREIGN PATENT DOCUMENTS

| | | |
|---|---|---|
| WO | WO 2004/032770 | 4/2004 |
| WO | WO 2005/007024 A2 | 1/2005 |

OTHER PUBLICATIONS

European Patent Office, Invitation to Pay Additional Fees and Communication Relating to the Results of the Partial International Search for International Application No. PCT/US2006/060019 dated Mar. 13, 2007.

European Patent Office, European Search Report for European Patent Application No. 08 16 5292, titled Surgical Access Port, dated Jul. 1, 2009.

\* cited by examiner

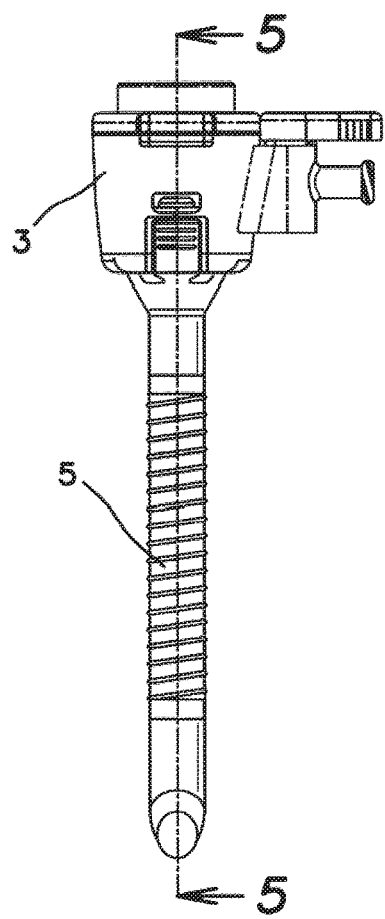
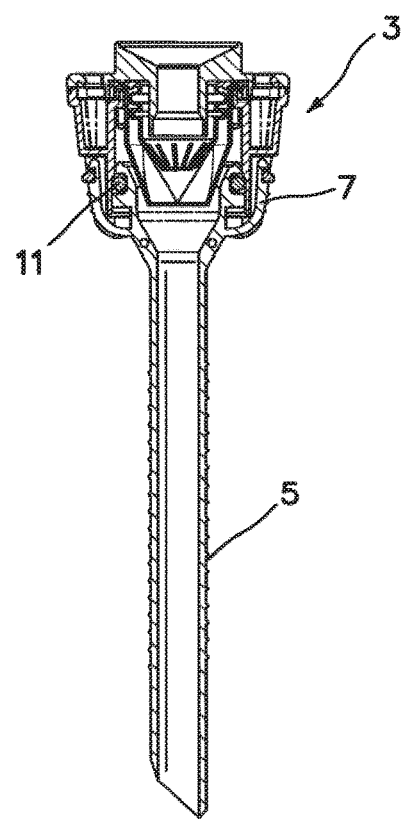
FIG. 4
FIG. 5

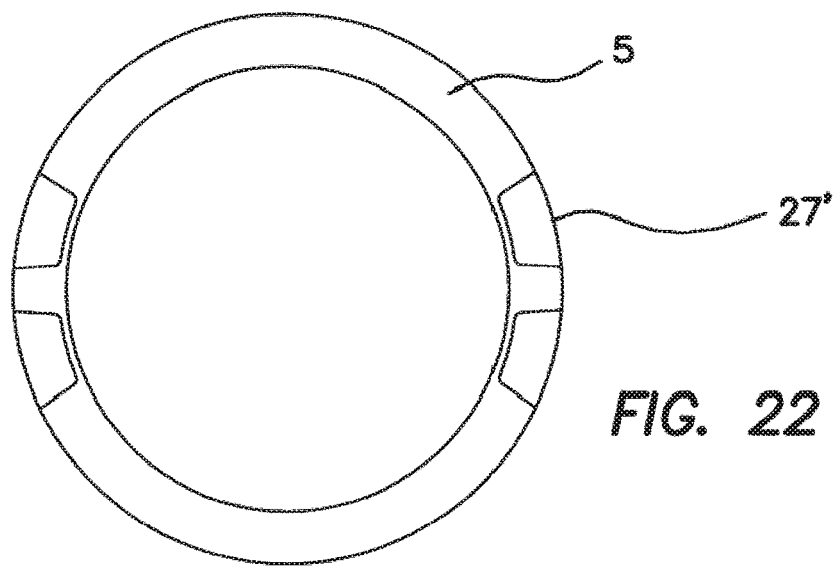
FIG. 22
FIG. 23
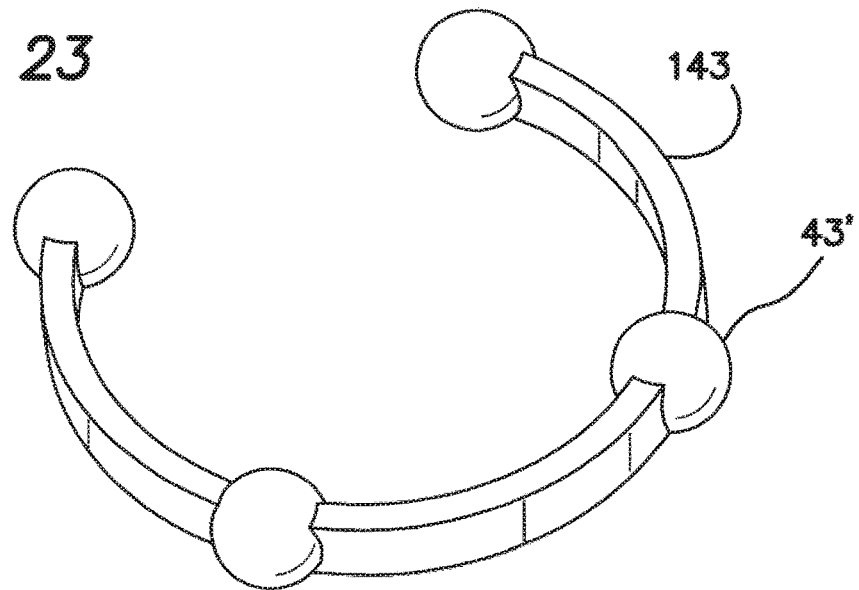

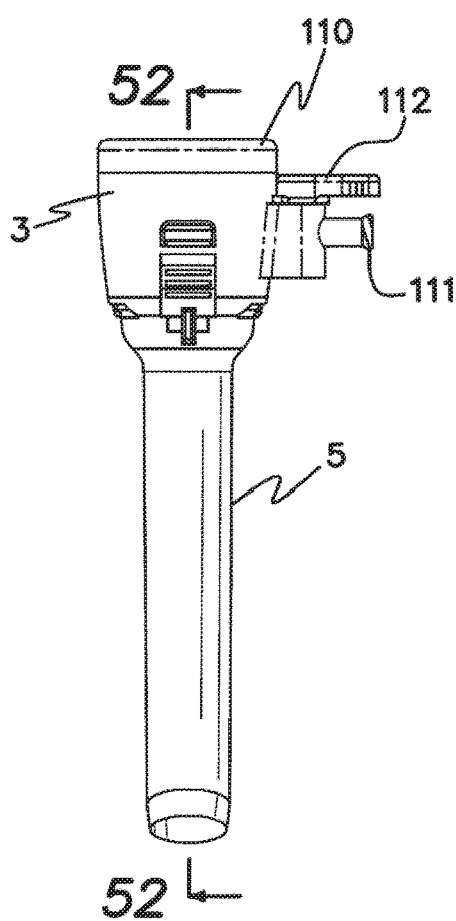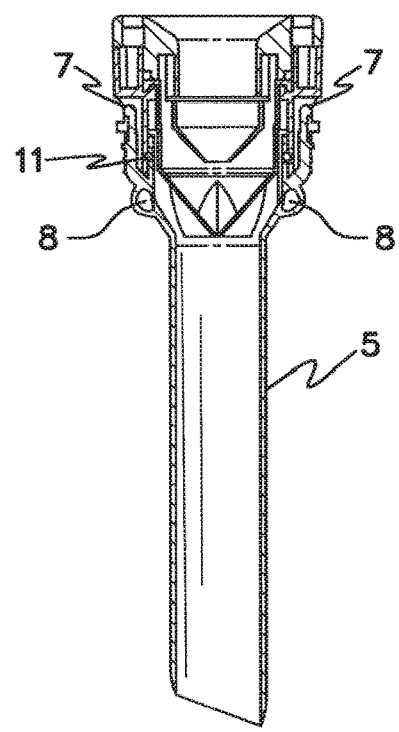
FIG. 51
FIG. 52

SURGICAL ACCESS PORT

CROSS-REFERENCE TO RELATED APPLICATIONS

This application is a continuation U.S. patent application Ser. No. 14/636,252 entitled "SURGICAL ACCESS PORT," filed Mar. 3, 2015, currently pending, which is a continuation of U.S. patent application Ser. No. 13/872,340 entitled "SURGICAL ACCESS PORT," filed Apr. 29, 2013, which issued as U.S. Pat. No. 8,968,250, which is a continuation of U.S. patent application Ser. No. 11/549,926 entitled "SURGICAL ACCESS PORT," filed Oct. 16, 2006, which issued as U.S. Pat. No. 8,430,851, which claims the benefit of U.S. Provisional Application Nos. 60/726,825, filed Oct. 14, 2005, and 60/828,515, filed Oct. 6, 2006, the disclosures of all of which are hereby incorporated by reference as if set forth in full herein.

BACKGROUND

Laparoscopic surgery is commonly performed using access ports or trocars, which provide instrument access across an abdominal wall and into a gas pressurized abdominal cavity. Trocar seals within the trocars allow instrument changes with no or minimal loss in gas pressure. Such seals should be very durable even when challenged by the insertion of sharp-pointed instruments. They should be capable of accommodating a wide range of inserted instrumentation without leaking. They should be nearly friction-free so that they do not interfere with the action of the instrument. And they should not damage the inserted instruments. In addition, they should be cost-effective and user-friendly, and not add to the complexity of a surgical procedure. Also, due to the inherent limited confines of laparoscopic surgery, a continuing effort to reduce facial defects and to reduce interference between trocars, smaller or compact trocars are desirable while still providing the above-noted functionalities or enhanced functionalities.

Laparoscopic surgery is an evolving modality. Significant changes in instrumentation continue to challenge the trocar seals presently in use. Accordingly, there remains a continuing need to extend the range, durability and sensitivity of trocar seals.

SUMMARY

Generally, the present invention provides surgical access port or trocar with a low-profile seal housing releasable from a cannula capable of accommodating an optical obturator. In one aspect, a surgical access port comprises a trocar seal housing having at least one seal, a trocar cannula having a lumen, the at least one seal arranged to seal the lumen and a trocar lock releasably connecting the trocar cannula to the seal housing and being one of slidably and pivotably connected to one of the trocar seal housing and trocar cannula.

In one aspect, a surgical access port comprises a trocar seal housing having an instrument seal, a zero seal and an alignment channel with a generally funneled entry. The zero seal is fixed to the trocar seal housing and the instrument seal is positioned between the alignment channel and the zero seal and is pivotably connected to the seal housing and a trocar cannula is attached to the trocar seal housing.

In one aspect, a surgical access port comprises a trocar seal housing having an instrument seal, a zero seal, a shield and an alignment channel with a generally funneled entry. The zero seal is fixed to the trocar seal housing, the instrument seal is positioned between the alignment channel and the zero seal and is connected to the seal housing. The shield is positioned between the alignment channel and the instrument seal and a trocar cannula is attached to the trocar seal housing.

Many of the attendant features of the present invention will be more readily appreciated as the same becomes better understood by reference to the foregoing and following description and considered in connection with the accompanying drawings in which like reference symbols designate like parts throughout.

BRIEF DESCRIPTION OF THE DRAWINGS

FIG. 4 is a side view of a surgical access port without an optical obturator in accordance with various aspects of the present invention;

FIG. 5 is a cross-sectional view taken along section lines 5-5 of FIG. 4 in accordance with various aspects of the present invention;

FIG. 22 is a top view of a portion of socket lock in accordance with various aspects of the present invention;

FIG. 23 is a perspective view of a socket lock in accordance with various aspects of the present invention;

FIG. 51 is a side view of a surgical access port without an optical obturator in accordance with various aspects of the present invention;

FIG. 52 is a cross-sectional view taken along section lines 52-52 of FIG. 51 in accordance with various aspects of the present invention;

DETAILED DESCRIPTION

Figure 1:
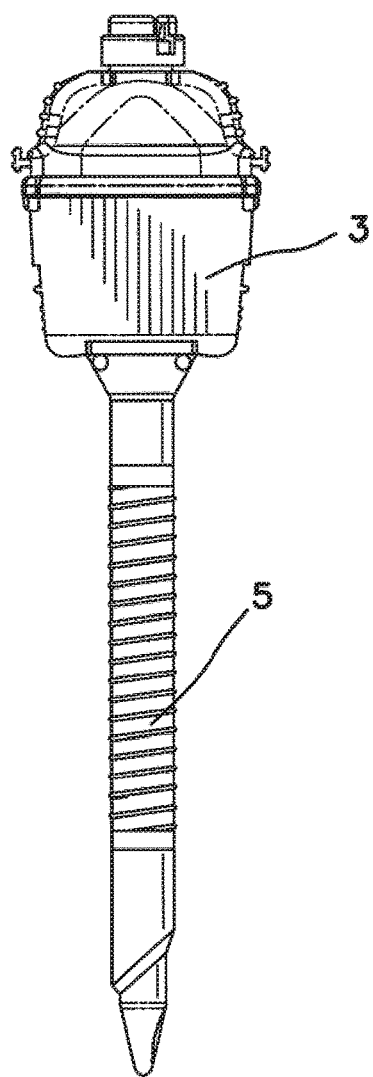
FIG. 1 is a front view of a surgical access port in accordance with various aspects of the present invention.
Figure 2:
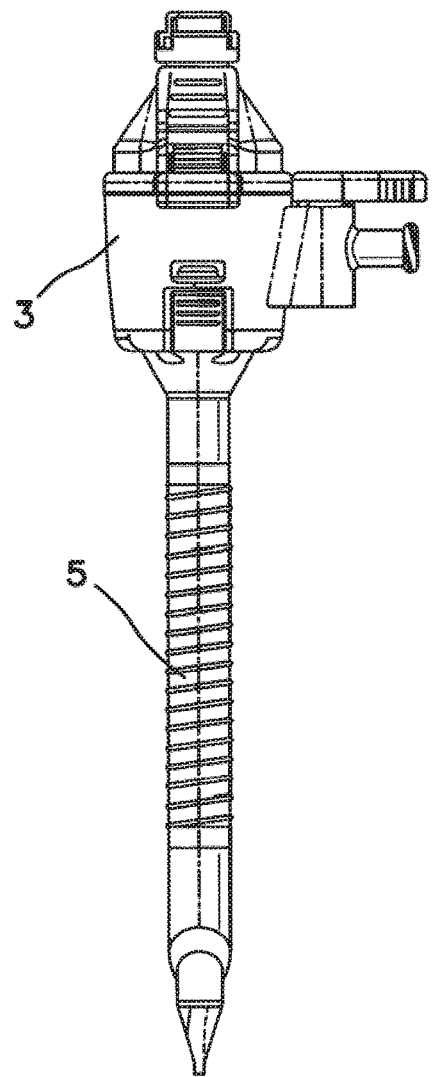
FIG. 2 is a side view of a surgical access port in accordance with various aspects of the present invention.
Figure 3:
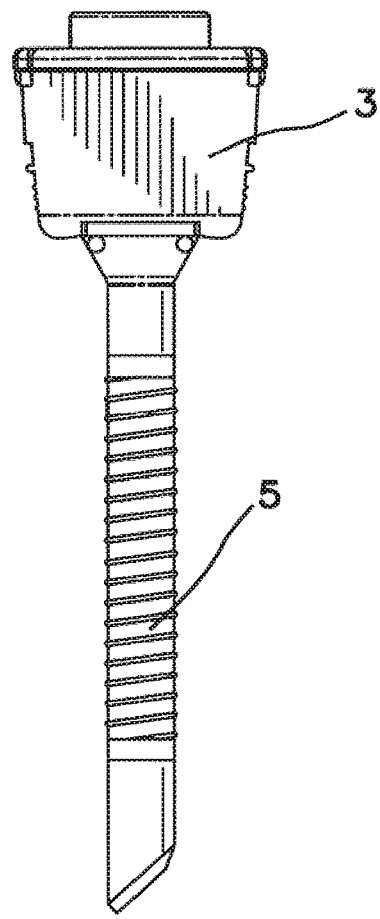
FIG. 3 is a front view of a surgical access port without an optical obturator in accordance with various aspects of the present invention.
Figure 6:
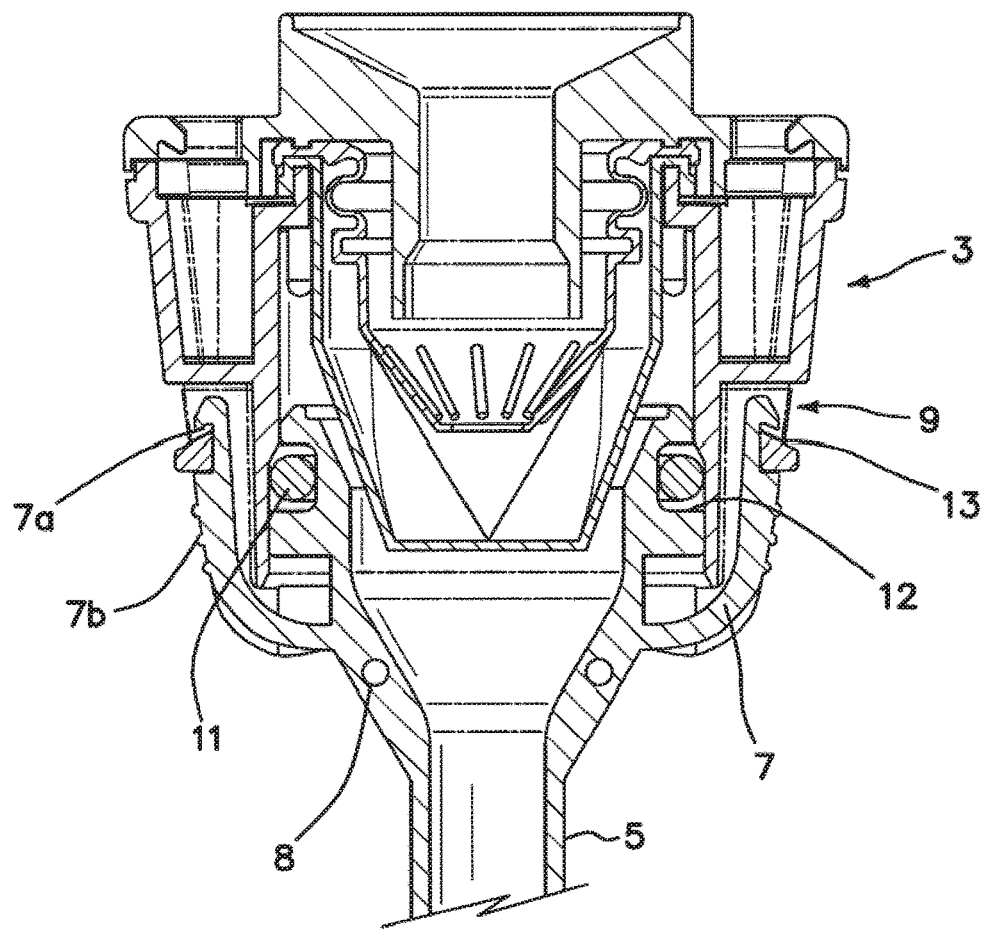
FIG. 6 is an enlarged cross-sectional side view of a surgical access port without an optical obturator in accordance with various aspects of the present invention.
Figure 7:
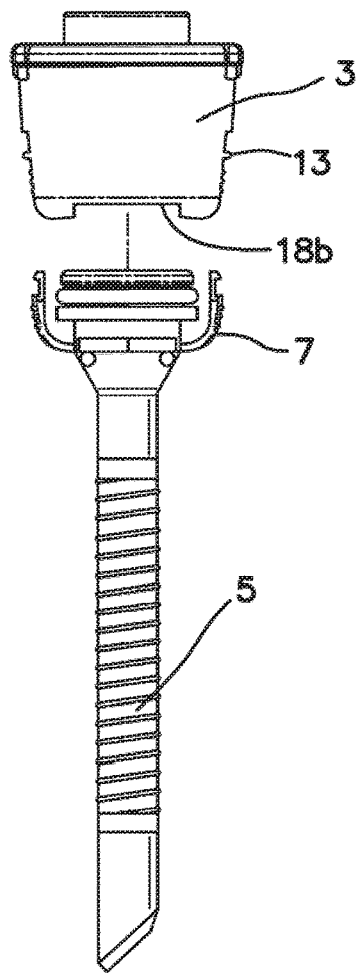
FIG. 7 is front view of a trocar seal housing detached from a trocar cannula in accordance with various aspects of the present invention.
Figure 8:
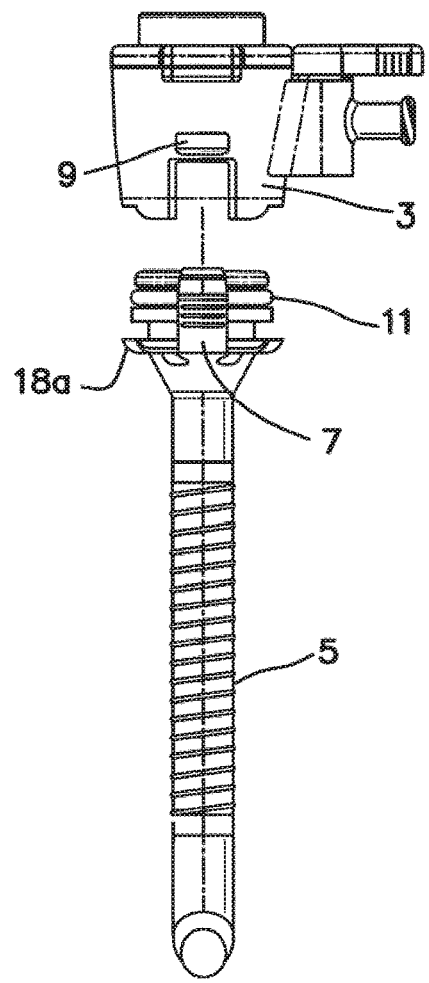
FIG. 8 is side view of a trocar seal housing detached from a trocar cannula in accordance with various aspects of the present invention.

A surgical access port, e.g., a trocar, which comprises a trocar seal housing, a trocar cannula, and/or an optical obturator is provided. In this description, "proximal" or "proximally" refers to that portion of the instrument, component, or element that extends toward the user. "Distal" or "distally" refers to that portion of the instrument, component, or element that extends away from the user. The trocar is configured to access a body cavity and to maintain positive pressure at its distal end to prevent loss of surgical insufflation gas such as carbon dioxide used, for example, in laparoscopic procedures to insufflate the body cavity. The trocar seal and trocar cannula is also configured to sealingly engage surgical instruments of various diameters, which would typically be inserted through the trocar, to prevent loss of surgical gas during use of such instruments. In one aspect, the trocar seal housing is releasably attachable to the trocar cannula to allow the seal to be removed during surgery to enable the extraction of tissue specimens through the trocar. The trocar in one aspect has or is included with an optical obturator having a tip, which includes a smooth outer surface and has a high degree of optical clarity.

Referring now to FIGS. 1-4, the trocar seal housing 3 in one aspect can be easily detached or removed from the trocar cannula 5 and easily attached or re-attached to the trocar cannula 5 for example during a surgical procedure. During surgery, small tissue specimens may be extracted from a body cavity through a trocar to enable pathological analysis of the tissue specimen. The integrity of the tissue specimen can be maintained or the maintenance facilitated by avoiding or minimizing withdrawal of delicate tissue specimens through a trocar seal. As such, in one aspect, the trocar seal housing 3 is arranged to be removed from the trocar cannula 5 to enable extraction of tissue specimens from a body cavity while maintaining the integrity of the tissue specimen. The trocar seal housing 3 also easily reattaches to the trocar cannula 5 after its initial removal during a surgical procedure.

Also, in one aspect, the trocar seal housing 3 is easily removable from the trocar cannula 5 to enable rapid desufflation of an insufflated body cavity. In one aspect, a trocar lock releasably attaches the trocar cannula to the trocar seal housing. For example, towards the end of a laparoscopic surgical procedure, release of the insufflation gas such as carbon dioxide from the peritoneal cavity of the patient is performed. By opening one or more stopcock valves on the trocar seal, desufflation can be achieved. The flow rate through the stopcock valves, however, can be slow with regard to evacuation of the carbon dioxide from the peritoneal cavity and therefore the time expended to evacuate the insufflation gas can be excessive. By removing the seal housing 3 from the cannula 5, the cannula provides an unobstructed outlet for the insufflation gas to escape thereby decreasing desufflation time.

In FIGS. 5-8, two cantilever arms 7 extend from the cannula 5 which engage mating slots 9 on the trocar seal housing 3. Each of the cantilever arms 7 has a hook 7a on its distal end, which engages a ledge 13 on the trocar seal housing 3 when the trocar seal housing 3 is attached to the trocar cannula 5. The hooks on the cantilever arms maintain the axial position of the trocar seal housing on the trocar cannula and prevent axial dislodgment of the trocar seal housing 3 from the trocar cannula 5.

The cantilever arms 7 in one aspect act as leaf springs resiliently attaching onto the trocar seal housing 3. For example, during attachment of the trocar seal housing 3 onto the trocar cannula 5, the cantilever arms 7 flex inward until the distal ends of the cantilever arms reach slots 9 in the trocar seal housing 3. Once the distal ends of the cantilever arms 7 reach the trocar seal housing slots 9, the cantilever arms 7 spring outward such that the hooks 7a overhang the mating ledges 13 on the trocar seal housing 3. When an axial force is applied to the trocar seal housing 3 relative to the trocar cannula 5, the hooks 7a further engage the ledges 13 on the trocar seal housing and do not allow removal of the trocar seal housing from the trocar cannula. As such, in one aspect, a trocar lock comprises a pair of resilient arms 7 extending from opposing sides of the trocar cannula 5 in a direction parallel to a longitudinal axis of the cannula. The pair of resilient arms operationally engaging the pair of slots 9 on opposing sides of the trocar seal housing 3.

To remove the trocar seal housing 3 from the trocar cannula 5, finger tabs 7b located on the mid-portion of the cantilever arms 7 are depressed causing the cantilever arms to move inward resulting in the disengagement of the hooks 7a from the housing ledges 13. The trocar seal housing 3 can thereby be removed from the trocar cannula 5 by applying an axial force to the trocar seal housing relative to the trocar cannula. The cantilever arms 7 on the trocar cannula 5 also prevent or resist rotation of the trocar seal housing relative to the trocar cannula 5. For example, the cantilever arms 7 prevent the trocar seal housing 3 from being twisted off of the trocar cannula 5 during manipulation of the trocar. In one aspect, the trocar seal housing 3 is prevented from being twisted off by tabs or extended portions 18a of the cannula 5 engaging recesses or slots 18b in the seal housing 3. The trocar seal housing and cannula attachment can also be threaded and/or bayonet lock connections to attach the trocar seal housing 3 to the trocar cannula 5. However, inadvertently rotating the trocar seal housing 3 relative to the trocar cannula 5 during manipulation of inserted instrumentation or manipulation of connected insufflation gas tubing to the seal housing may result in an unintended detachment of the trocar seal housing 3 from the trocar cannula 5. An unintended detachment of a trocar seal housing from a trocar cannula during a surgical procedure may result in a loss of insufflation gas, a loss of visibility of the operative area, a delay in the procedure, and/or other potential surgical issues.

The trocar cannula 5 in one aspect has a cannula seal or sealing ring 11 positioned in a groove, cavity or gland 12 at its proximal end which forms a seal with the inside diameter of the trocar seal housing. In one aspect, a gland is an o-ring cavity and includes the portion of the cavity, e.g., portions of the trocar cannula and/or housing, that compress the o-ring to create a seal. In one aspect, the groove 12 in a proximal end of the cannula substantially encircles an outer periphery of the cannula 5 and a seal or the sealing ring 11 is disposed in the groove 12. The sealing ring 11, which in one aspect comprises of an o-ring with an "o" cross section, prevents loss of pneumoperitoneum between the trocar seal housing 3 and the trocar cannula 5. To minimize the friction between the sealing ring 11 and the trocar seal housing 3, an x-ring can be used rather than an o-ring. The x-ring has a generally "x" cross section and minimizes the area of contact between the sealing ring and the trocar seal housing 3 resulting in a reduction of static and kinetic frictional forces. Reducing the frictional forces between the sealing ring 11 and the trocar seal housing 3 reduces the axial force utilized to attach and/or detach the trocar seal relative to the trocar cannula 5.

Figure 9:
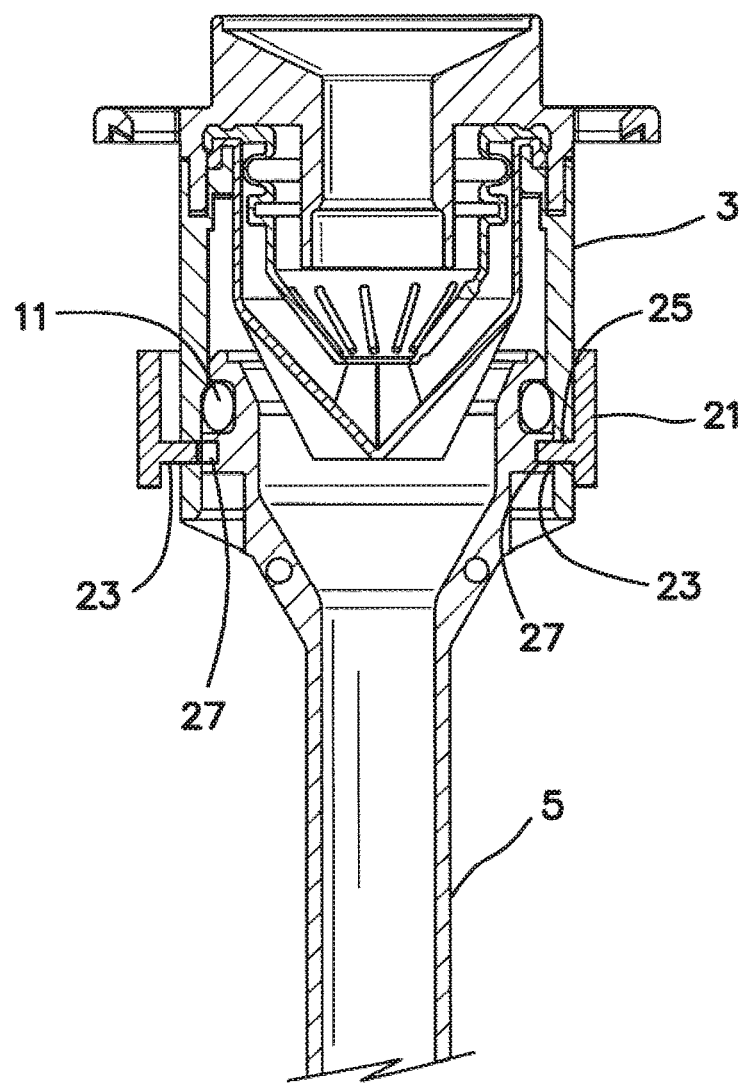
FIG. 9 is a cross-sectional side view of a surgical access port without an optical obturator in accordance with various aspects of the present invention.
Figure 10:
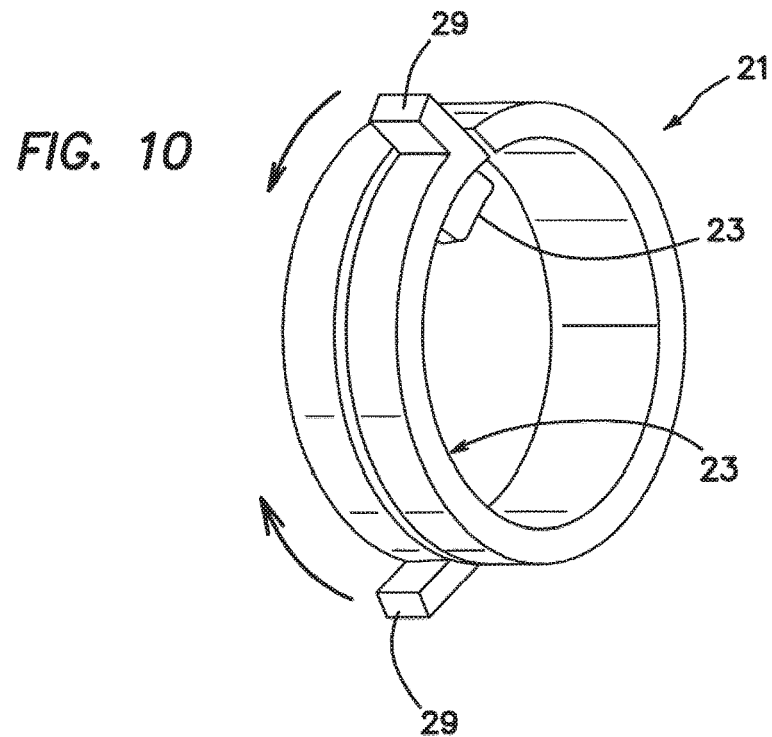
FIG. 10 is a perspective view of a lock ring in accordance with various aspects of the present invention.
Figure 11:
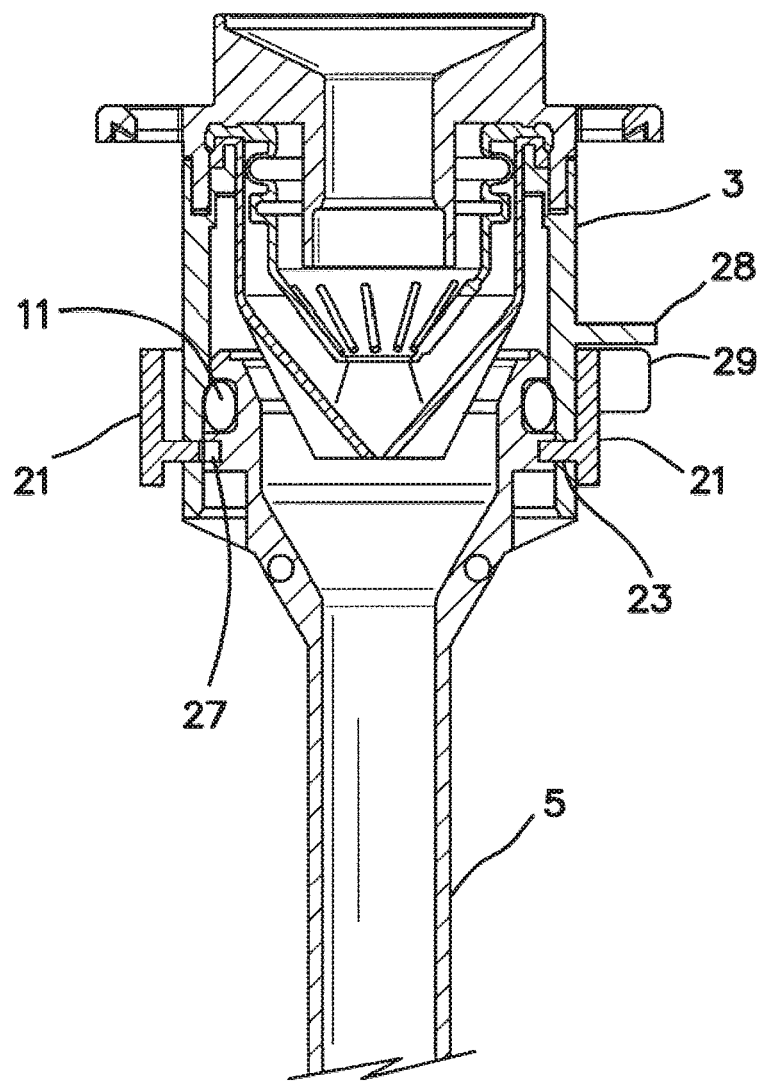
FIG. 11 is a cross-sectional side view of a surgical access port without an optical obturator in accordance with various aspects of the present invention.

Referring now to FIGS. 9-11, a trocar lock ring 21 releasably connects the trocar seal housing 3 to the trocar cannula 5. The lock ring 21 is shown simultaneously in an unlocked position on the left side of the trocar seal housing and a locked position on the right side of the trocar seal housing 3 for simplicity and ease of discussion. The trocar lock ring 21 in one aspect is substantially cylindrical and outlines a perimeter that generally corresponds to the outer periphery of the trocar seal housing 3. The lock ring 21 positions the trocar seal housing between the lock ring and the trocar cannula. One or more projections, protrusions or tabs 23 extend from the lock ring 21. In one aspect, one or more rectangular tabs extend perpendicularly from an inner surface of the lock ring 21 and the longitudinal axis of the trocar cannula 5. In a lock position, the tabs 23 extend through a corresponding aperture or slot 25 in the trocar seal housing 3 and into a corresponding groove or cavity 27 in the trocar cannula 5 thereby securing the trocar seal housing 3 to the trocar cannula 5. The groove 27 in the trocar cannula is adjacent to, e.g., below or away from the proximal end of the trocar cannula 5, the groove 12 in the trocar cannula holding the cannula seal 11. By moving or withdrawing the tab 23 out of the groove 27 in the trocar cannula 5, i.e., moving the lock ring 21 into an unlock position, the trocar seal housing 3 is released or allowed to be removed from the trocar cannula 5. In one aspect, the tab 23 is completely movable out of the groove 27 of the trocar cannula 5, but is not completely movable out of the corresponding aperture 25 in the trocar seal housing 3. As such, in one aspect, a trocar lock comprises a ring 21 having a tab 23 inwardly extending towards a center of the ring 21. The trocar seal housing 3 has an aperture 25 and the trocar cannula having a groove 27. The tab or tabs are movable from a first position in which the tab is engaged with the aperture, sized to receive the tab, in the trocar seal housing 3 and a second position in which the tab is engaged with the aperture in the trocar seal housing and the groove, sized to receive the tab, in the trocar cannula 5.

In one operational case, the lock tab 23 protrudes through the wall of the trocar seal housing 3 and into the trocar cannula groove 27, locking the trocar seal housing 3 to the trocar cannula 5. To release the trocar seal housing 3 from the trocar cannula 5, the locking ring 21 is manipulated in specific predetermined manner to prevent accidental operation or unlocking of the trocar seal housing 3 from the trocar cannula 5. The manipulation of the locking ring 21 causes the lock tab 23 to be directly or indirectly withdrawn from the groove 27, thus allowing removal of the trocar seal housing 3 from the trocar cannula 5.

The locking ring in one aspect is arranged with external grip tabs 29 flushed with or extended on an outer surface of the lock ring 21 and positioned on opposing sides of the ring. The grip tabs 29 in one aspect are also positioned on the outer surface of the lock ring 21. In one operation, squeezing the tabs 29 together in the direction shown deforms the lock ring 21 to a generally oval shape manipulates the locking ring and causes withdrawal of the tabs 23 from the groove 27. The grip tabs 29 in one aspect are protected from accidental operation by being positioned under a ledge 28 projecting from the trocar seal housing 3.

Figure 12:
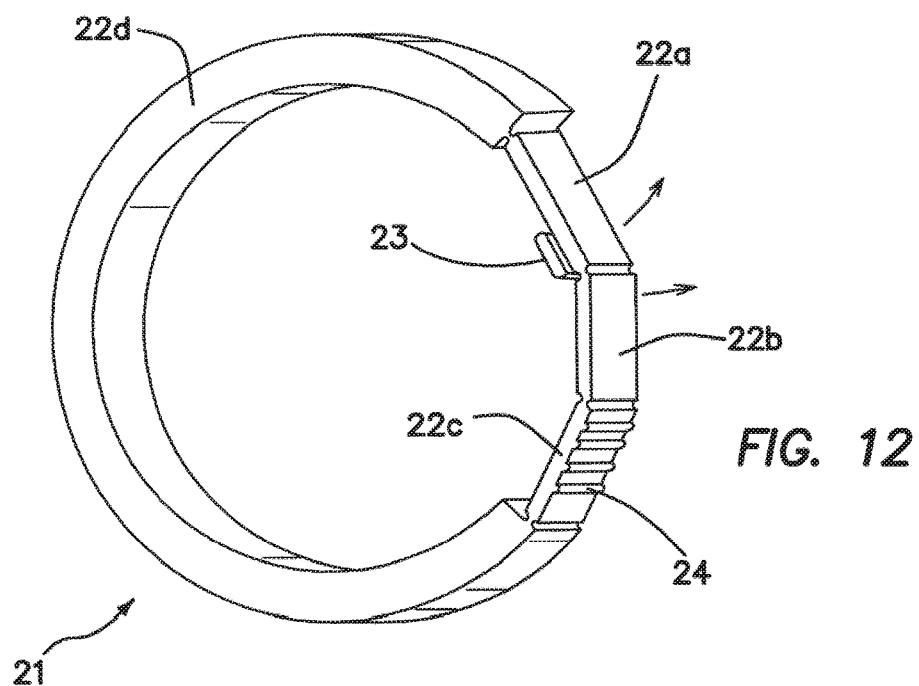
FIG. 12 is a perspective view of a lock ring in accordance with various aspects of the present invention.

In one aspect, as shown in FIG. 12, the locking ring 21 is generally cylindrical and close-fitting to the trocar seal housing 3 with the locking ring 21 having one or more sections forming a portion of the cylinder. One or more projections or tabs 23 extend from the one or more sections of the locking ring 21 towards the seal housing 3. In one aspect, a portion of the locking ring 21 has three sections 22a,b,c each connected successively to each other via living hinges, walls having curved cavities allowing the sections to move away from the center of the locking ring 21. One of the sections, section 22a is connected to the remaining portion 22d of the locking ring 21 at about a mid-point of the remaining portion 22d and another section, section 22c is connected to another end of the remaining portion 22d of the locking ring 21 near the external or outer surface of the locking ring 21. The other section, section 22b is connected between the two sections, sections 22a and 22c. One of the sections, section 22a has a projection or tab 23 extending perpendicularly from the section towards the seal housing 3 to engage the seal housing aperture 25 and the cannula groove 27. The other section, section 22c, has grip tabs 24 extending from an outer surface of the section 22c. In one operation, as shown by the direction arrows, by squeezing one of the sections, e.g., section 22c, inwards towards the center of the locking ring 21 causes the adjoining two sections, sections 22a,b to move or rotate outwards away from the seal housing 3 and cannula 5, thereby pulling or withdrawing the tab 23 from the cannula groove 27. As such, the trocar seal housing 3 is unlocked or can be removed from the trocar cannula 5.

Figure 13:
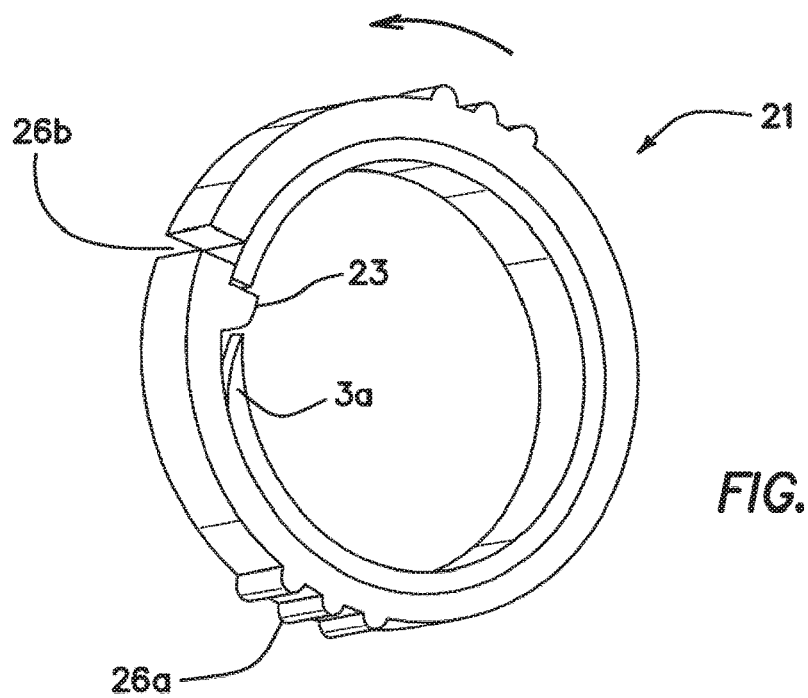
FIG. 13 is a perspective view of a lock ring in accordance with various aspects of the present invention.
Figure 14:
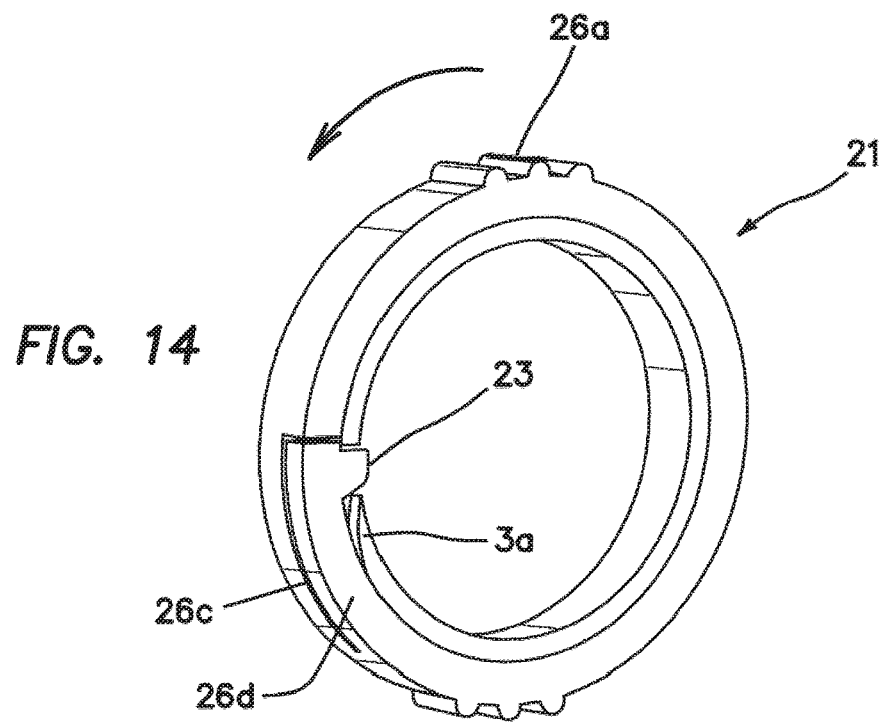
FIG. 14 is a perspective view of a lock ring in accordance with various aspects of the present invention.

In FIGS. 13-14, in one aspect, the locking ring 21 is rotatable closely around the seal housing 3. The locking ring 21 has an axial split 26b and one or more lock tabs 23 extending from the locking ring 21. The axial split provides for an easily molded part with a single element per ring and allows the ring 21 to flex and thereby facilitate rotation. The seal housing 3 in one aspect has a ramp 3a adjacent to the seal housing aperture 25 to facilitate rotation and thus withdrawal of the tab 23. Grip tabs 26a extending along a portion or portions of the external surface of the locking ring 21 facilitates manipulation of the locking ring 21. The lock ring in one aspect is arranged with multiple local slots or slits 26c that create or act as a leaf spring 26d to flexibly hold or bias the lock tabs 23 towards the seal housing aperture 25 and cannula groove 27.

Figure 15:
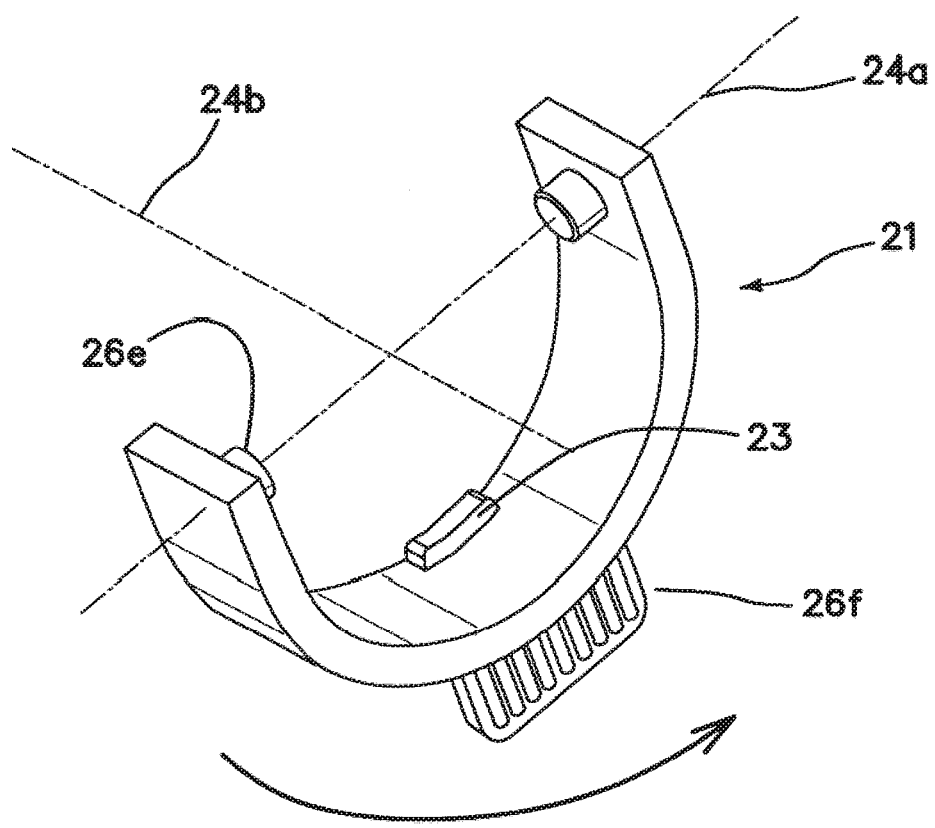
FIG. 15 is a perspective view of a lock ring in accordance with various aspects of the present invention.

In FIG. 15, the lock ring 21 in one aspect pivots or tips about an axis 24a perpendicular to the main or longitudinal axis 24b of the trocar cannula 5. One or more pivot pins 26e extend from or into the locking ring 21 connecting the lock ring 21 to the seal housing 3 and providing pivot points and a pivot axis generally perpendicular to the longitudinal axis 24a of the trocar cannula 5. As the lock ring pivots or tips, as shown by the direction arrow, for example, the lock tabs 23 extending therefrom engage or withdraw the trocar cannula groove 27 and seal housing aperture 25. A grip tab 26f extending from the external surface of the locking ring 21 assists in manipulating the ring 21. In one aspect, a plurality of lock rings and associated tabs and grips or a combination of lock rings described above are used to releasably secure the trocar seal housing 3 to the trocar cannula 5. As such, in one aspect, a trocar lock comprises a ring 21 having a tab 23 inwardly extending towards a center of the ring 21. The trocar seal housing 3 has an aperture 25 and the trocar cannula having a groove 27. The tab or tabs are movable from a first position in which the tab is engaged with the aperture, sized to receive the tab, in the trocar seal housing 3 and a second position in which the tab is engaged with the aperture in the trocar seal housing and the groove, sized to receive the tab, in the trocar cannula 5.

Figure 16:
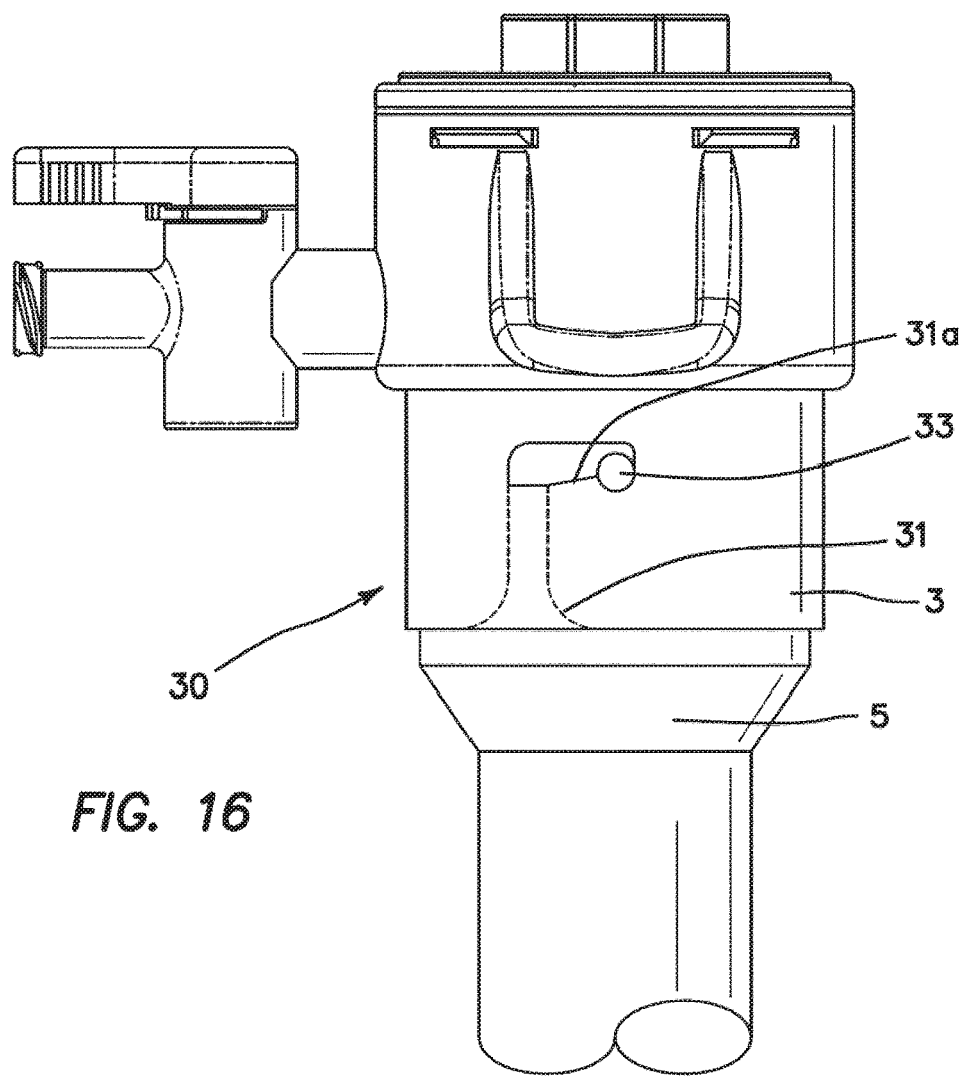
FIG. 16 is a side view of a surgical access port without an optical obturator and partially shown cannula in accordance with various aspects of the present invention.
Figure 17:
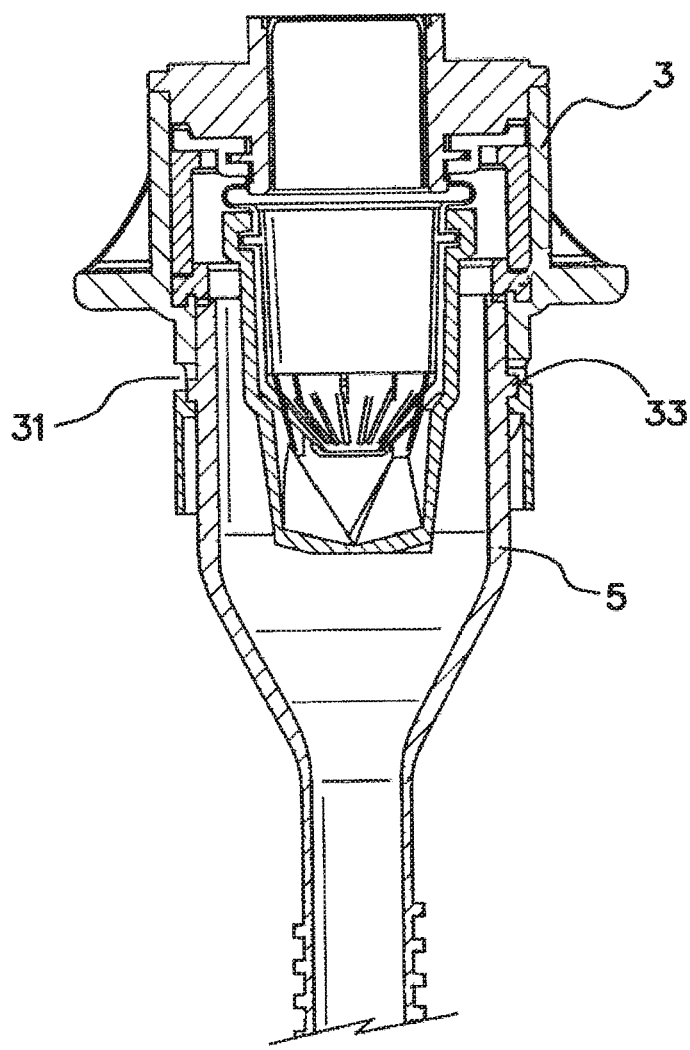
FIG. 17 is a cross-sectional side view of a surgical access port without an optical obturator and partially shown cannula in accordance with various aspects of the present invention.
Figure 18:
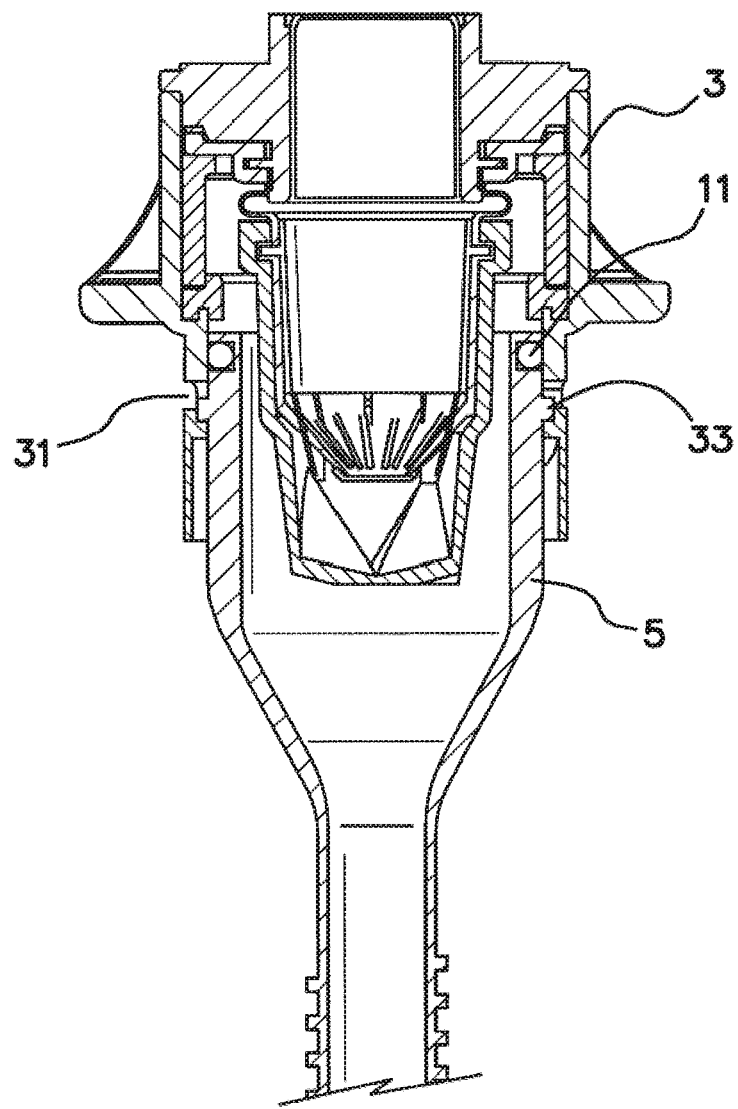
FIG. 18 is a cross-sectional side view of a surgical access port without an optical obturator and partially shown cannula in accordance with various aspects of the present invention.

Referring now to FIGS. 16-18, the trocar cannula 5 with a seal 11, such as an o-ring or x-ring, e.g., an elastomeric ring with an x-shaped cross-section, situated in a groove 12 in the cannula 5 with a releasable bayonet lock 30 is shown. The cannula 5 also has one or more pins or tabs 33 that project radially out from an external surface of the cannula away from the longitudinal axis of the cannula 5. The pins 33 engage slots 31 in the seal housing such that as the pins move within the slots, the cannula is rotated (approximately 90° or a quarter of one revolution). Once the cannula 5 has been turned, the pins 33 are surrounded top and bottom, thus locking the cannula 5 to the seal housing 3. The slots 31 in one aspect starts with a ramped or curved opening extending parallel to the longitudinal axis of the cannula and curving towards a generally horizontal direction into a ramped end 31a with a small detent at the end of the ramp.

A cannula seal in one aspect is arranged such that it is axially compressed as the cannula rides up the ramp 31a. This adds friction, which helps prevent the cannula 5 and seal housing 3 from becoming separated unintentionally. However, with the added friction, having to overcome this friction can cause removal of the trocar seal housing from the trocar cannula to be difficult. A bayonet type attachment without additional friction, such as provided by axial seal compression, can reduce the effectiveness of preventing unintended detachment of the seal housing 3 from the cannula 5 during surgery as the instruments are manipulated through the trocar.

Figure 19:
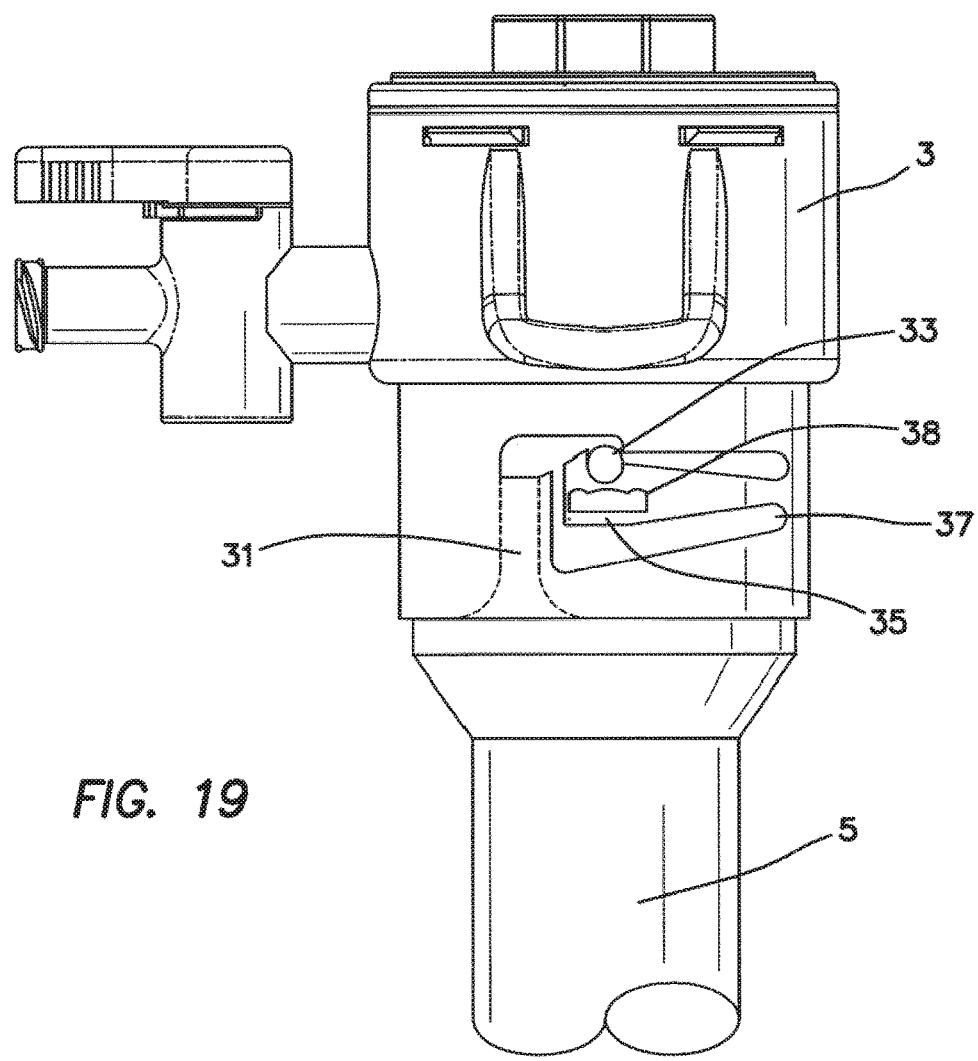
FIG. 19 is a side view of a surgical access port without an optical obturator and partially shown cannula in accordance with various aspects of the present invention.
Figure 20:
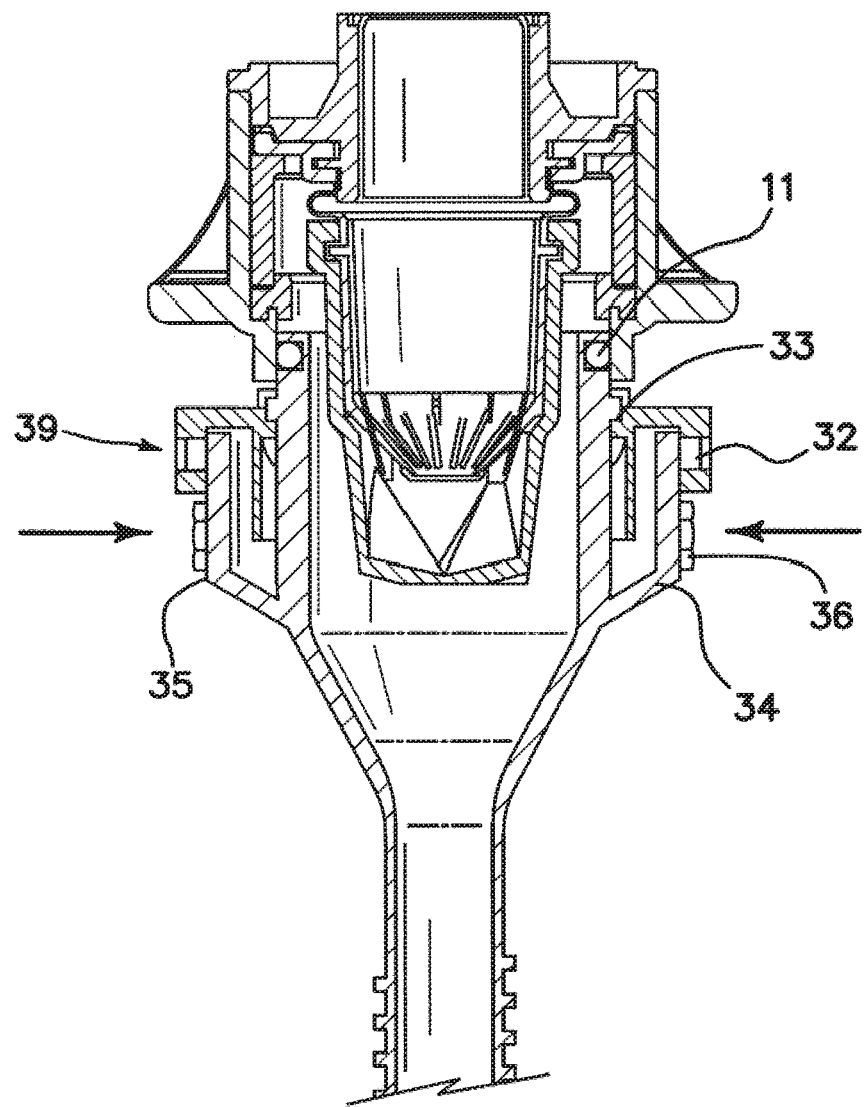
FIG. 20 is a cross-sectional side view of a surgical access port without an optical obturator and partially shown cannula in accordance with various aspects of the present invention.

In FIG. 19, the lock tab 35 prevents or resists rotation of the seal housing 3 and thus guards against unintended detachment of the seal housing 3 from the trocar cannula 5. As such, the lock tab 35 is manipulated before the seal housing can be rotated and detached. In one aspect, the lock tab 35 is arranged as a leaf spring integral to the seal housing 3 with a grip tab 38 extending from the outer surface of the lock tab 35. The lock tab 35 has a cavity arranged to engage the pin 33 extending from the trocar cannula 5 thereby securing the trocar seal housing 3 to the cannula 5. The lock tab 35 is deflected distally, e.g., pivoted, towards slot 37 in the seal housing to move the tab 35 out of the path of the pin 33 extending from the cannula 5. With the lock tab 35 out of the path of the pin, the seal housing can be rotated and removed from the cannula. As such, in one aspect, a trocar lock comprises a post or pin 33 extending from an external surface of the trocar seal cannula. A slot or slots 31,37 are in the trocar seal housing and a resilient arm or lock tab 35 in the trocar seal housing 3 is adjacent to the slot or slots. The lock tab 35 is movable towards or in a longitudinal direction. As shown in FIG. 20, the lock tab 35 in one aspect comprises a plurality of leaf spring latches 34 integral to the cannula 5 having one or more projections or tabs 32 also extending from the cannula 5. The latches are releasably engagable with the apertures or slots 39 in the seal housing 3. The latches 34 are squeezed towards each other, as shown for example by the direction arrows, using grip tabs 36 moving the projections 32 out of the slots 39 in the seal housing 3 and thereby allowing the seal housing to rotate and be removed from the cannula 5.

Figure 21:
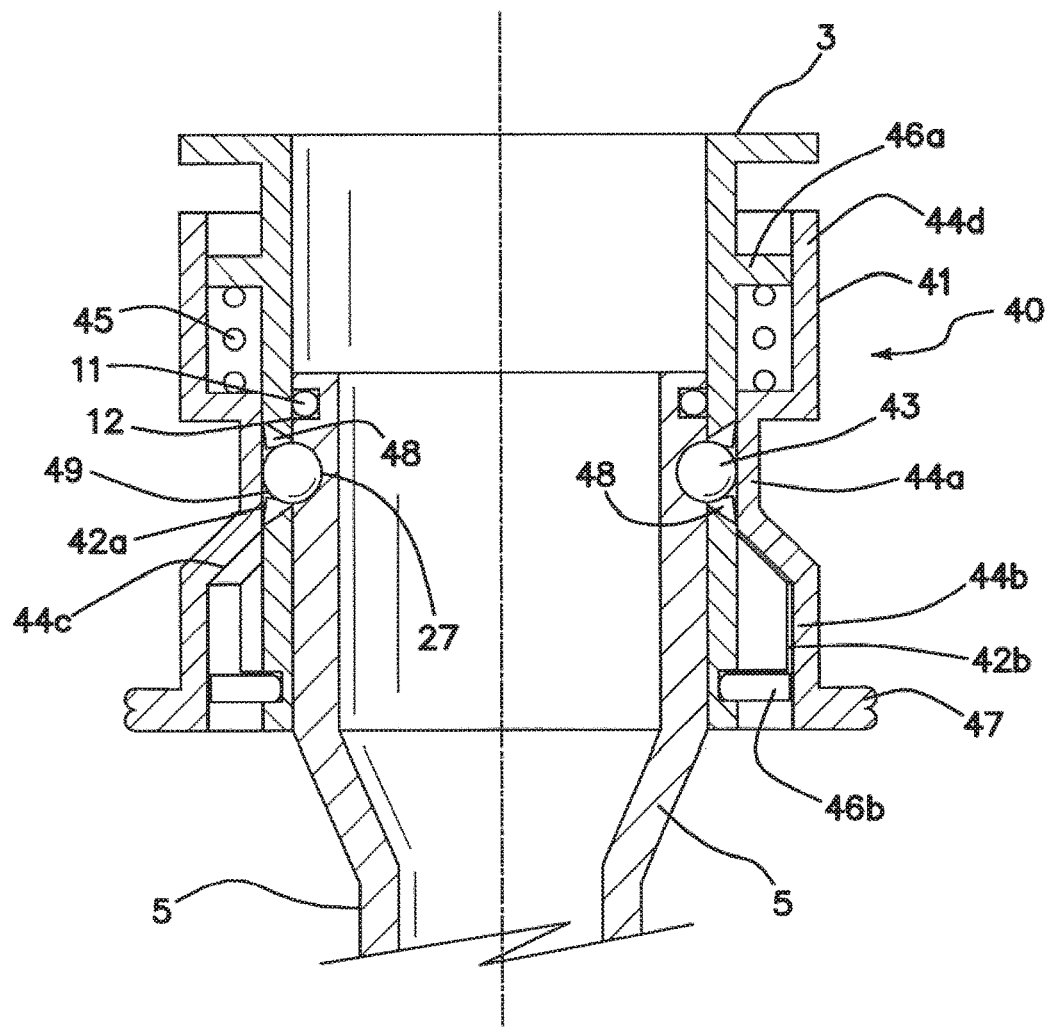
FIG. 21 is a cross-sectional side view of a surgical access port without an optical obturator and partially shown cannula in accordance with various aspects of the present invention.

Referring to FIG. 21, the trocar cannula 5 with a seal 11, such as an o-ring or x-ring, situated in a groove 12 in the cannula with a releasable socket lock 40 is shown. In one aspect, the cannula 5 has a plurality of apertures or slots or similarly situated groove 27 adjacent to the sealing groove 12 in the cannula 5. Socket lock 40 engages the apertures or groove in the cannula 5 to releasably secure the trocar seal housing 3 with the cannula 5.

In one aspect, the socket lock 40 comprises a plurality of generally circular or cylindrical beads or balls 43. One or more balls 43 protrude through the seal housing 3 and into the cannula groove 27, securing the trocar seal housing 3 to the trocar cannula 5. The balls 43 are held in position by a close fit collar 41. The collar 41 is arranged with two inside diameters 42a,b such that when the collar 41 is moved axially, the balls 43 are free to retract into the larger of the two inside diameters 42b, freeing the attachment of the seal housing 3 from the cannula 5. In one aspect, the collar is generally cylindrical having a first proximal portion 44a with a first diameter 42a and a second distal portion 44b with a second diameter 42b. The first diameter 42a generally corresponds to the diameter of the proximal end of the cannula and is smaller than the second diameter 42b. The second portion 44b is farther away from the proximal end of the cannula 5 than the first portion 44a of the collar 41. The collar 41 in one aspect comprises a ramp 44c connecting the two portions 44a,b and thus the inside diameters 42a,b which assists or facilitates the balls from moving or driving inwardly to the locked position when the collar is moved back to the original position. A return spring 45 axially in-line with a longitudinal axis of the trocar cannula 5 and connected to collar 41 provides a force to bias the collar towards the lock position thereby providing protection against unintended operation and automatic closure or locking of the seal housing 3 onto the cannula 5. As such, in one aspect, the trocar lock comprises a collar 41 and a plurality of balls 43 connected to the collar 41. The balls 43 are engagable with corresponding apertures in the trocar seal housing 3 and the trocar cannula 5. A return spring 45 connected to the collar 41 biases the collar 41 towards a distal end of the trocar cannula 5.

In one aspect, a third or additional proximal portion 44d of the collar 41 along with projections 46a from the seal housing 3 secure the return spring 45 to the collar and the seal housing 3. A retainer 46b, such as a snap or split ring, in conjunction with the second or distal portion 44b of the collar 41 secures the collar 41 to the seal housing 3 and the balls 43 when positioned in contact with the second portion 44b. Grip tabs 47 in one aspect extend from an outer periphery of the collar to facilitate manipulation of the collar 41. Ramps or cuts 48 adjacent to or part of the apertures 49 of the seal housing 3 facilitate movement of the balls 43 into the locking position or engagement with the seal housing 3.

Figure 24:
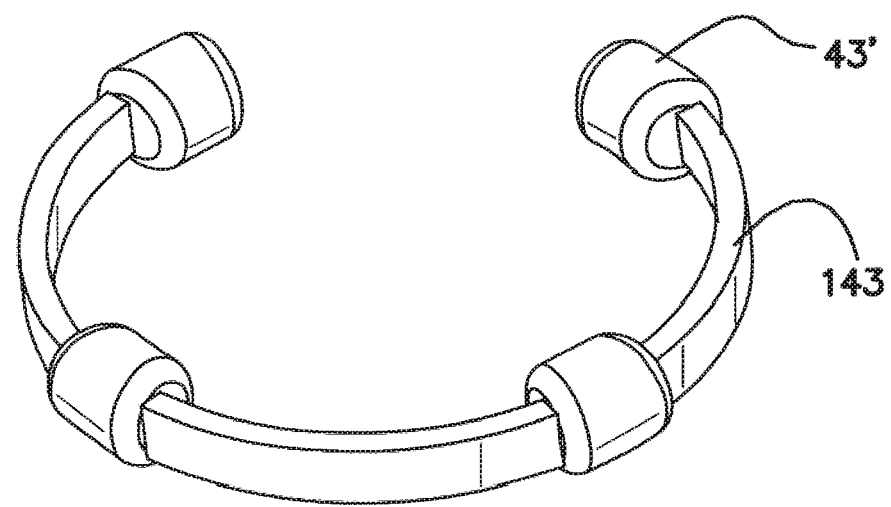
FIG. 24 is a perspective view of a socket lock in accordance with various aspects of the present invention.

In one aspect, the balls 43 are loose secured between the collar 41 and seal housing 3. The balls 43 are spaced from each other along a perimeter around the cannula to provide additional strength and reduce unwanted motion. The lock balls 43 in one aspect are spherical, cylindrical, barrel-shaped or otherwise curved. The balls in one aspect are equally spaced or irregularly or randomly spaced. Positioning the balls towards each other, for example, providing two sets of two balls, however can assist in plastic molding operations as this eliminates or reduces the need for slides, which can simplify the mold of the trocar cannula 5 with apertures 27' as shown in FIG. 22. In one aspect, the balls are provided as a molded ring 143 incorporating generally spherical, cylindrical, barrel-shaped or generally curved components 43' movable as loose balls as shown in FIGS. 23-24. Such a molded ring can reduce cost and aid in assembly operations. As such, a ring 143 in one aspect connects the plurality of balls 43 to each other.

Figure 25:
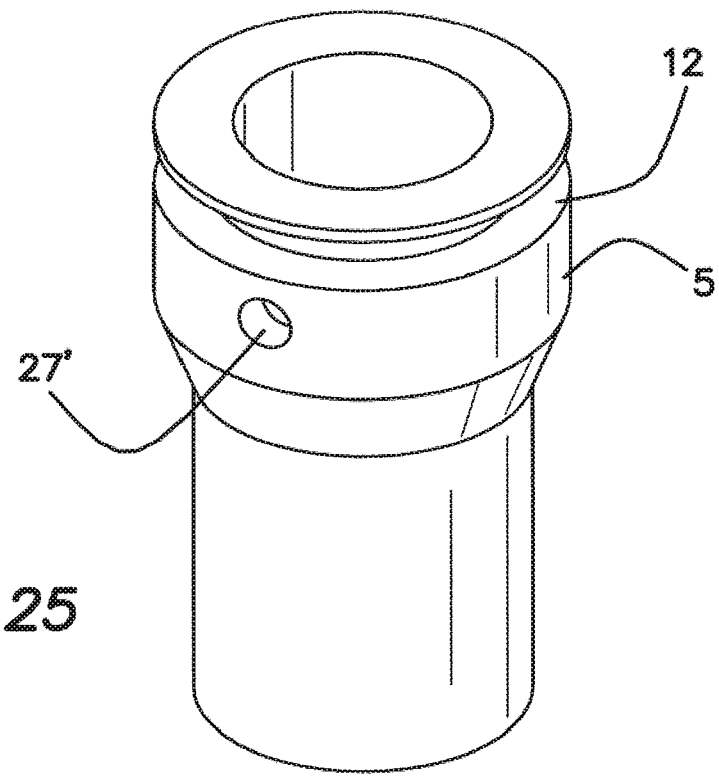
FIG. 25 is a perspective view of a partially shown trocar cannula in accordance with various aspects of the present invention.

In one aspect, the socket lock 40 engages a plurality of discrete apertures 27' in the cannula 5 as shown in FIG. 25 instead of a continuous groove 27. As such, the balls 43 when engaged with the apertures 27' would be locked rotationally as well as axially. However, a continuous groove avoids having to orientate or align the lock with the cannula to first mate the components together.

Figure 26:
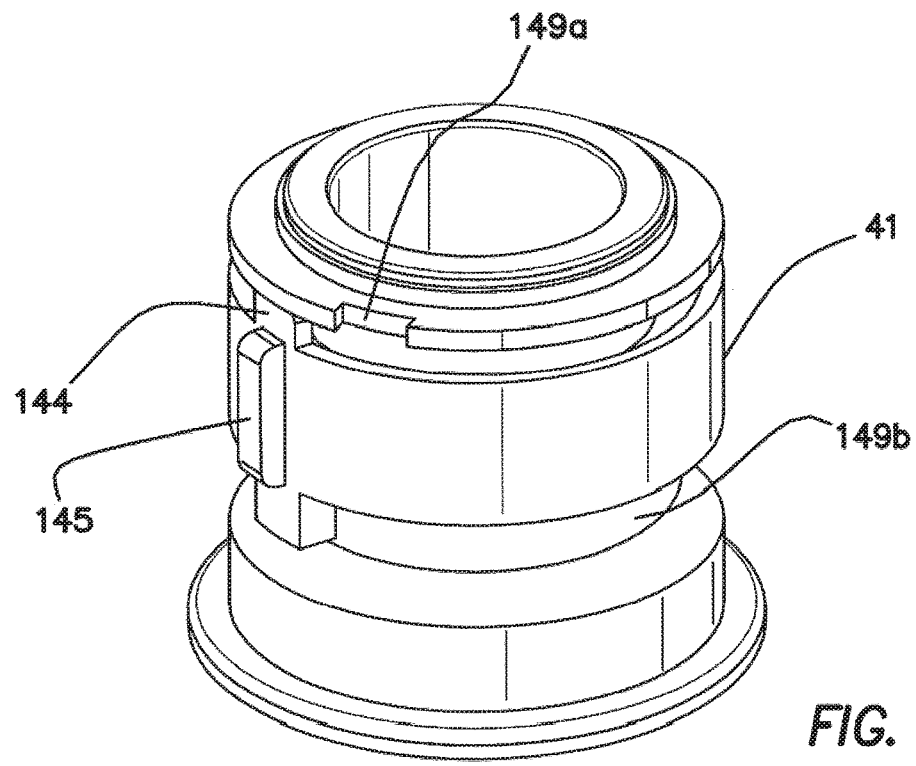
FIG. 26 is a perspective view of a trocar seal housing and socket lock in accordance with various aspects of the present invention.

In one aspect, to protect against unintended operation, a second motion is utilized before the collar 41 is retracted axially. As such, in one aspect, a latch is depressed before the collar 41 can be moved and, in one aspect, the collar 41 is first rotated before being able to be withdrawn axially. In FIG. 26, the collar 41 has one or more tabs 144 extending from the collar parallel to the longitudinal axis of the cannula 5. The collar 41 travels or rotates within a groove or channel 149b to engage/disengage slots 149a in the seal housing 3 or a slots 149a in a ledge extending from the outer periphery of the seal housing 3. In one aspect, the groove 149b extends along the periphery of the collar 41. As such, to first activate the release or unlocking of the seal housing 3 from the trocar cannula 5, the collar 41 is rotated to align the tabs 144 with the slots 149a to allow axial movement of the collar 41. Axially movement of the collar 41 subsequently allows the releasing of the seal housing 3 from cannula 5. Grip tabs 145 in one aspect extending from the collar 41 in-line or adjacent to the tabs 144 facilitate movement of the collar 41.

Figure 27:
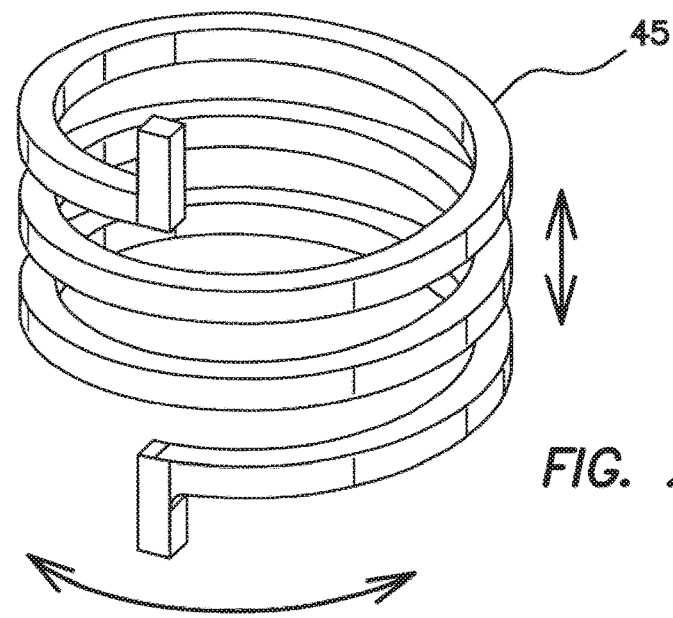
FIG. 27 is a perspective view of a return spring in accordance with various aspects of the present invention.

In one aspect, the return spring 45 also acts as a torsion spring when the collar is rotated before it can be retracted. For example, the spring is of a wound wire construction or a molded plastic part. In one aspect, the return spring 45 comprises a single large coil spring providing two biases, axially and rotationally, as shown for example by the direction arrows in FIG. 27 or multiple springs arranged axially at intervals around the inside of the collar. Multiple springs in one aspect are arranged to deflect sideways when the collar is rotated, thus acting as a torsional return spring.

Figure 28:
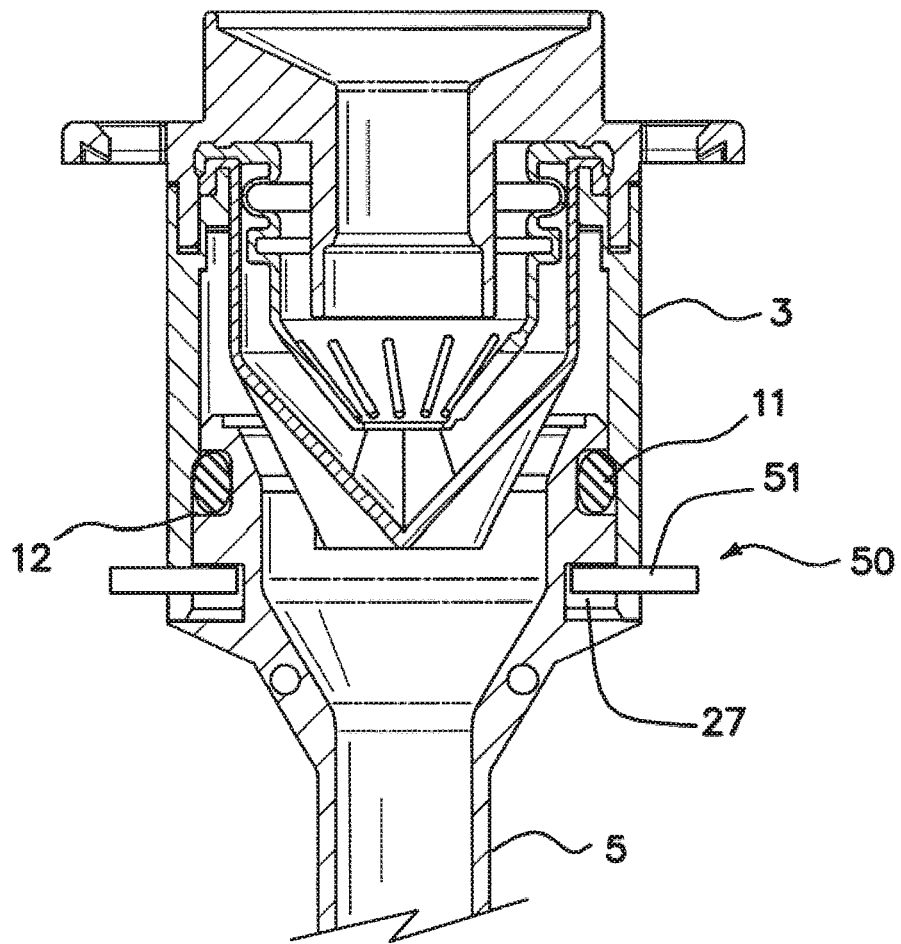
FIG. 28 is a cross-sectional side view of a surgical access port without an optical obturator and partially shown cannula in accordance with various aspects of the present invention.
Figure 29:
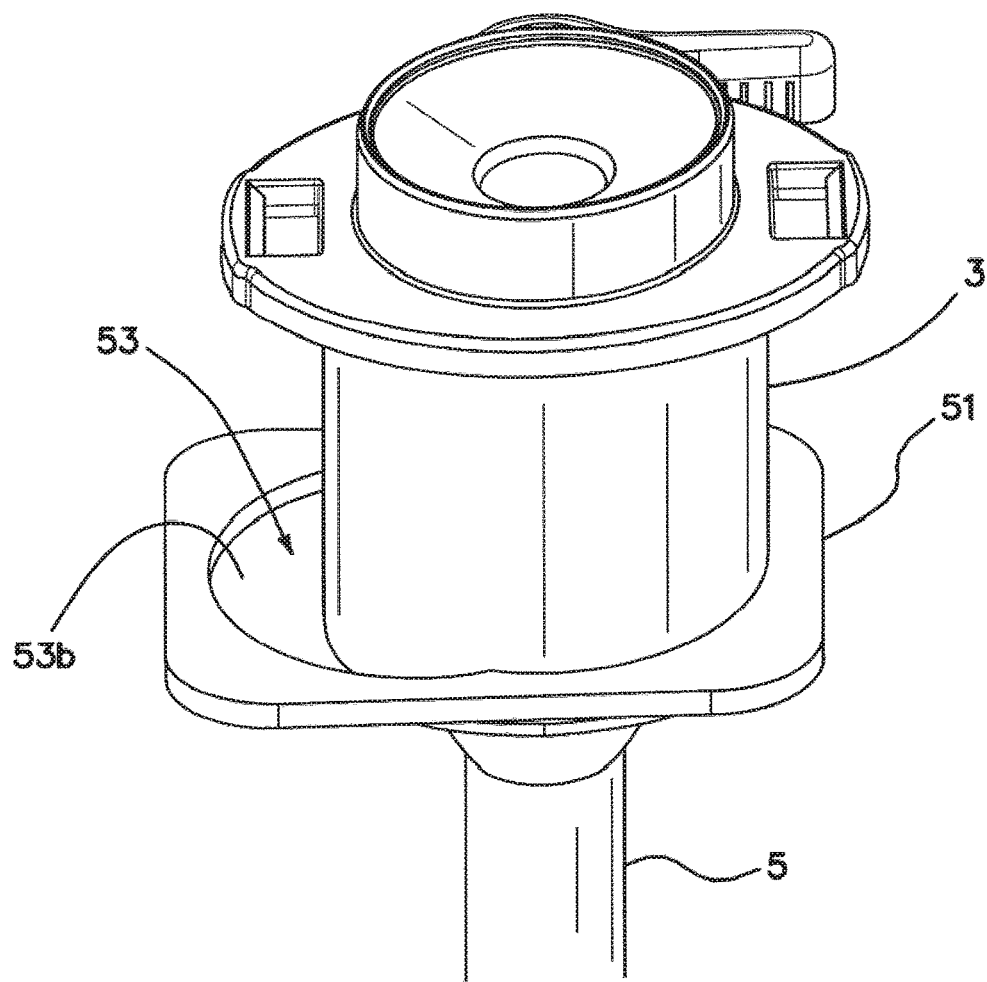
FIG. 29 is a perspective view of a surgical access port in a locked condition without an optical obturator and partially shown cannula in accordance with various aspects of the present invention.
Figure 30:
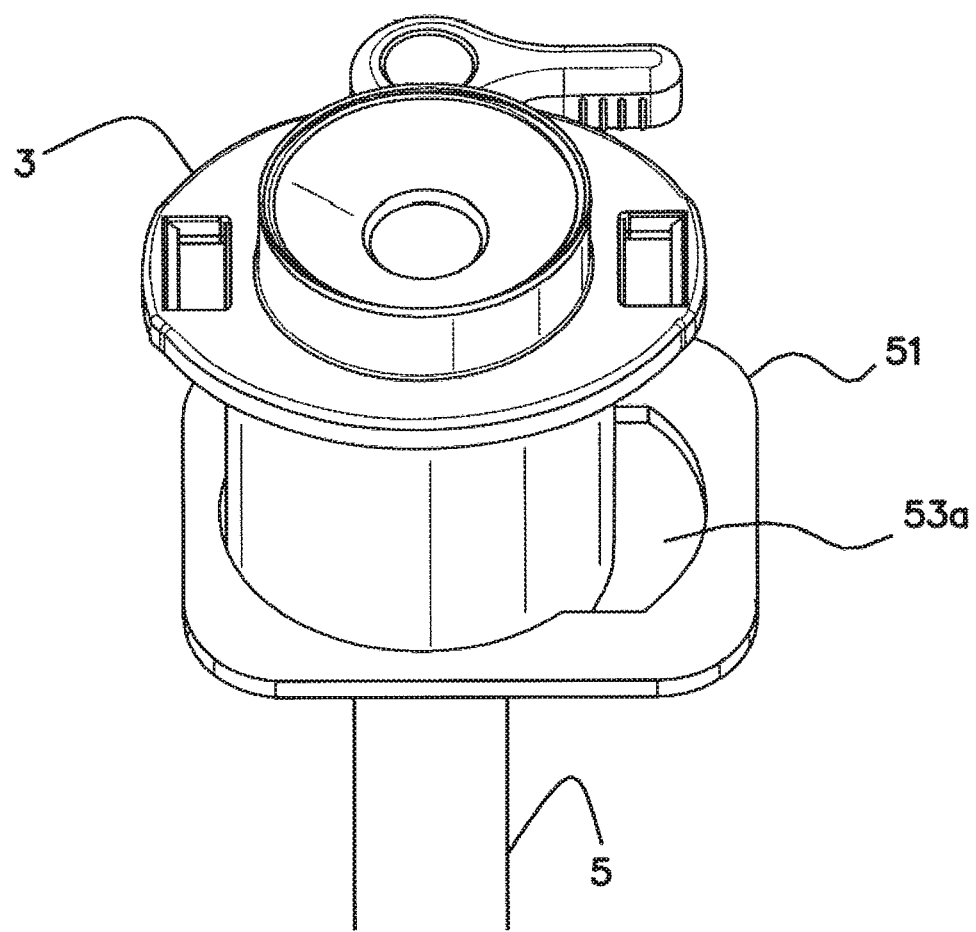
FIG. 30 is a perspective view of a surgical access port in an unlocked condition without an optical obturator and partially shown cannula in accordance with various aspects of the present invention.

Referring to FIGS. 28-30, the trocar cannula 5 with a seal 11, such as an o-ring or x-ring, situated in a groove 12 in the cannula 5 with a gate lock 50 is shown. In one aspect, the gate lock 50 engages a pair of parallel grooves 27 in the cannula 5. The gate lock 50 is a generally flat plate 51 with a keyhole-shaped aperture 53 through the plate. The keyhole-shaped aperture has a narrow portion 53a and wide portion 53b. As such, in one aspect, the trocar gate lock 50 comprises a substantially flat plate 51 having a keyhole slot 53 with a first aperture 53a being smaller than a second aperture 53b. The gate lock 50 slides from side to side in relation to the longitudinal axis of the trocar cannula 5. When the narrow portion 53a of the gate lock 50 engages the trocar seal housing 3, portions of the flat plate 51 or substantially planar tabs extending from the plate engage the groove 27 in the trocar cannula 5 thereby securing the trocar seal housing 3 to the trocar cannula 5. By moving or sliding the gate lock 50 in the opposite direction or extreme, the narrow portion 53a of the gate lock disengages the trocar cannula 5 as the seal housing 3 is positioned in the wide portion 53b of the gate lock 50. The gate lock 50 remains engaged with the trocar seal housing 3 via, for example, a groove or slot, but is removed or withdrawn from the groove 27 in the trocar cannula 5. Thus, the seal housing 3 can be removed from the trocar cannula 5. As such, the flat plate of the gate lock 50 in one aspect is movable in a direction perpendicular to a longitudinal axis of the trocar cannula from a first position in which the trocar seal housing is within the first aperture 53a and a second position in which the trocar seal housing is within the second aperture 53b. The flat plate 51 being in the first position engages with an aperture in the trocar seal housing 3 and the groove in the trocar cannula 5 and in a second position in which the flat plate 51 is engaged only with the aperture in the trocar seal housing 3.

Figure 31:
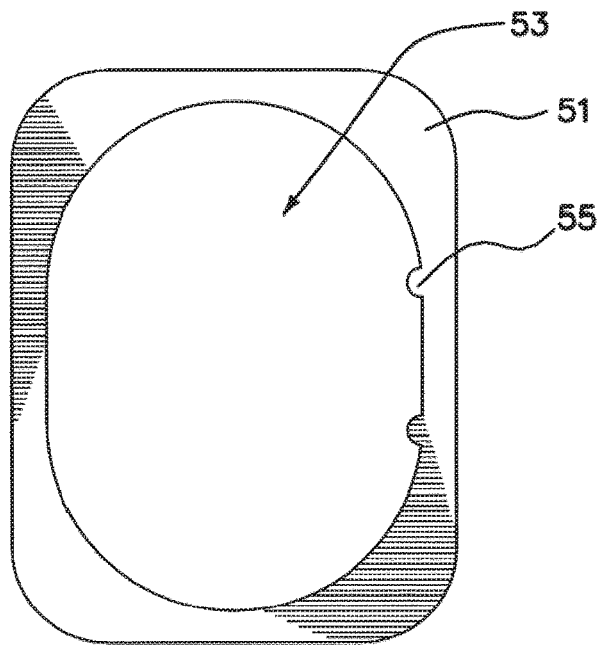
FIG. 31 is a top view of a gate lock in accordance with various aspects of the present invention.

In one aspect, the gate lock 50 is fitted with a return spring or detents to bias the gate lock 50 to one position, e.g., locked, versus another position, e.g., unlocked. In one aspect, the aperture 53 in the gate lock is generally round or oval in shape with one or more projections or detents 55 extending to the center of the gate lock as shown in FIG. 31.

Figure 33:
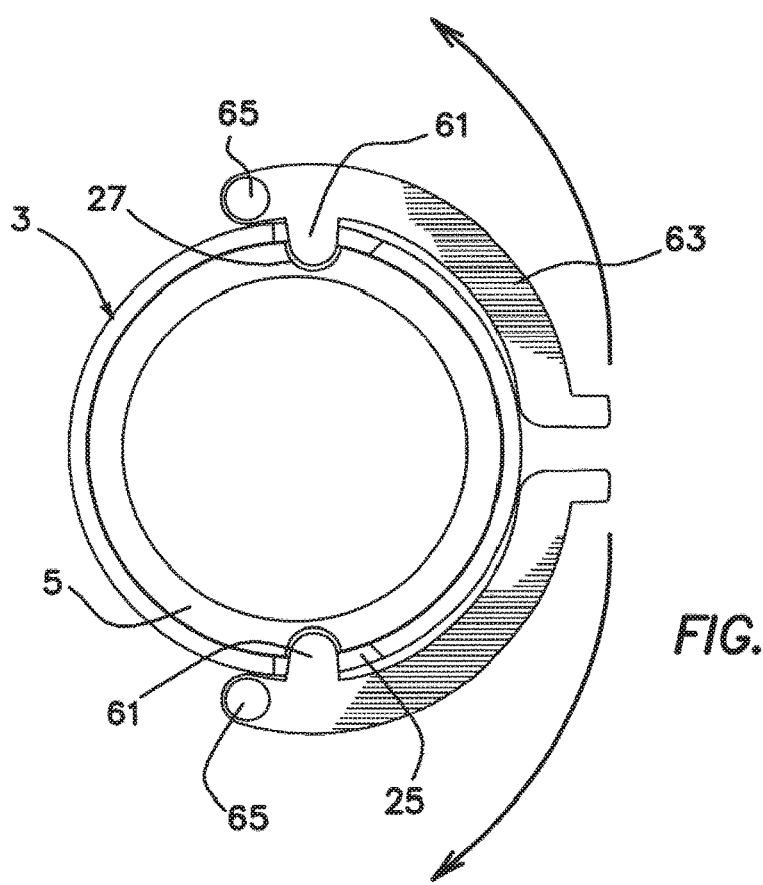
FIG. 33 is a cross-sectional top view of a surgical access port without an optical obturator and partially shown cannula in accordance with various aspects of the present invention.
Figure 32:
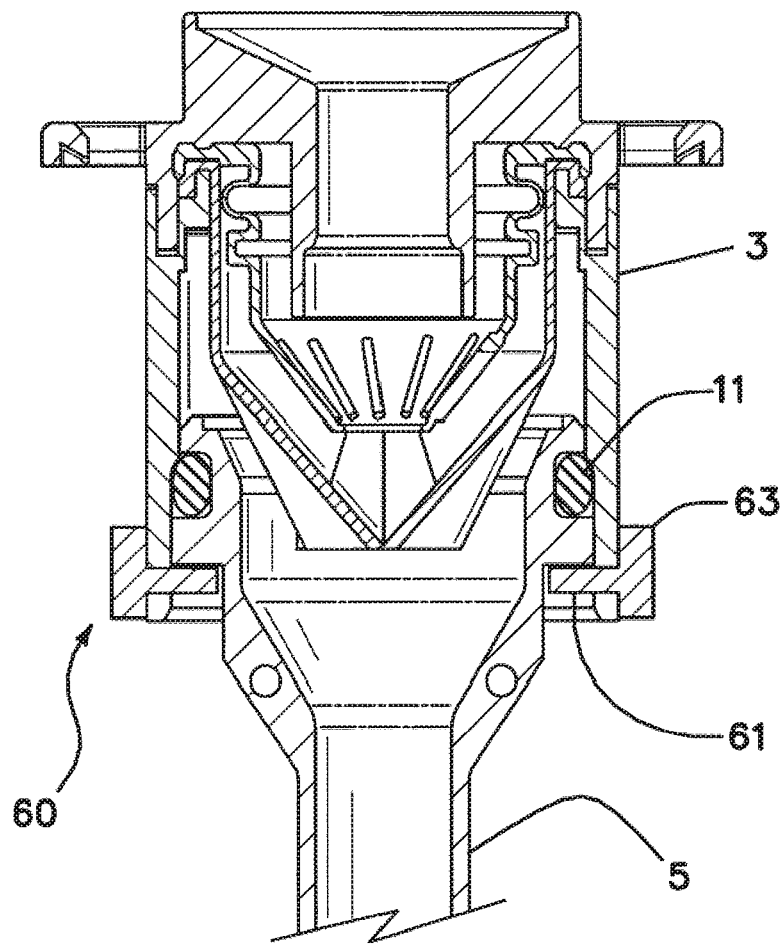
FIG. 32 is a cross-sectional side view of a surgical access port without an optical obturator and partially shown cannula in accordance with various aspects of the present invention.
Figure 34:
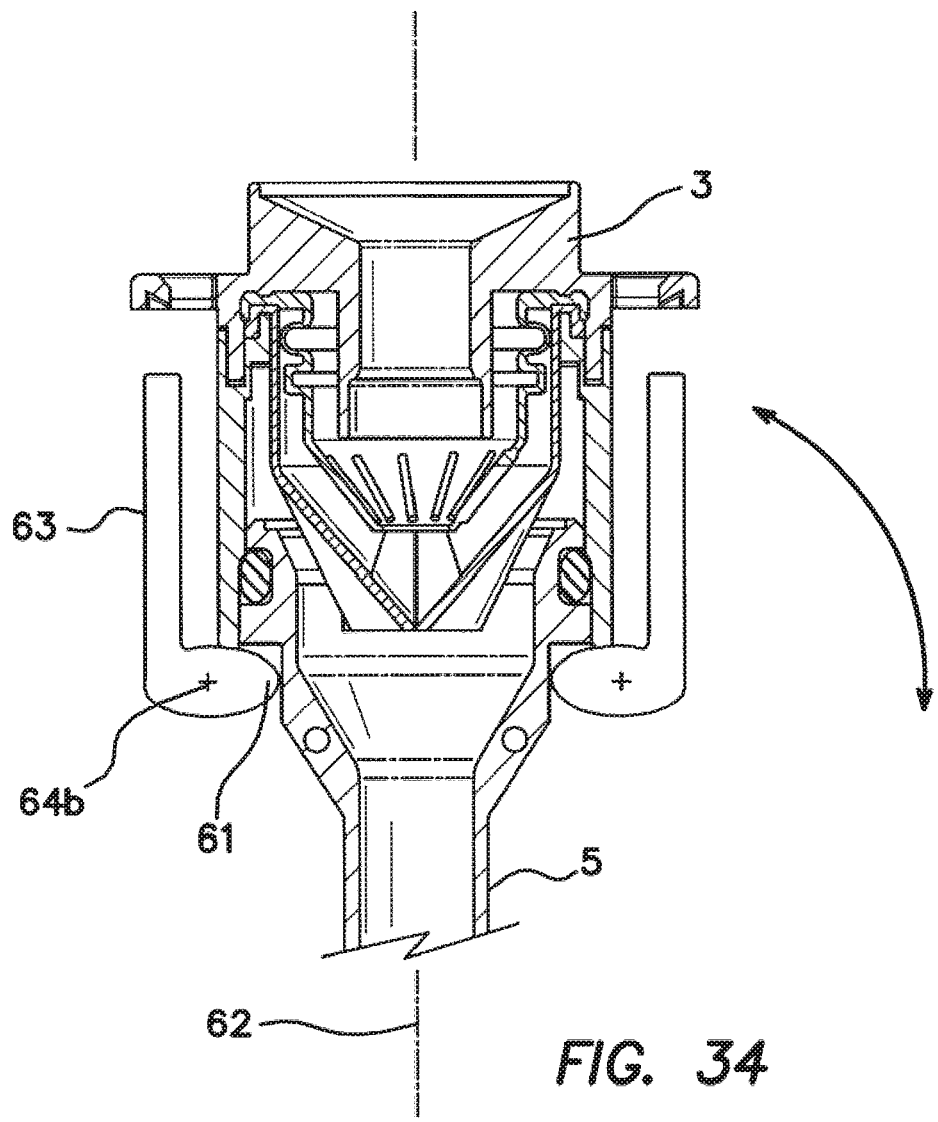
FIG. 34 is a cross-sectional side view of a surgical access port without an optical obturator and partially shown cannula in accordance with various aspects of the present invention.
Figure 35:
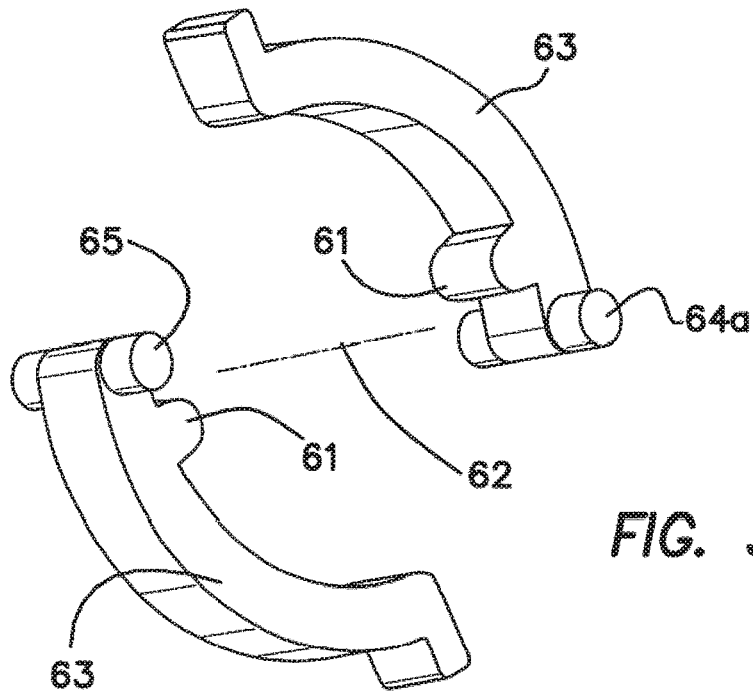
FIG. 35 is a perspective view of lock levers in accordance with various aspects of the present invention.

Referring to FIGS. 32-33, the trocar cannula 5 with a seal 11, such as an o-ring or x-ring, situated in a groove 12 in the cannula 5 with a lever lock 60 is shown. In one aspect, the lever lock 60 engages a groove or slots 27 in the cannula 5 to secure the seal housing 3 to the cannula 5. The lever lock 60 has one or more lever arms 63 with one or more projections or tabs 61 operationally engaged with a corresponding groove or slots 27 in the trocar cannula 5. The trocar seal housing 3 has a corresponding apertures or slots 25 extending through a sidewall of the trocar seal housing 3. The tab 61 of lever lock 60 when engaged with the groove 27 in the trocar cannula 5 through the slot in the seal housing 3 secures the trocar seal housing to the cannula 5. The lever arms 63 are attached to the seal housing via a pivot pin 65 extending from/to one end of the lever arms 63 to/from the seal housing 3. Rotating or pivoting the lever lock from out of a substantially horizontal position as shown for example by the direction arrows causes the tab 61 of arm 63 to withdraw from the groove 27 in the trocar cannula 5 and/or the aperture 25 in the trocar seal housing 3. Thus, the seal housing 3 can be released from the trocar cannula 5. In one aspect, the lever arms 63 are arranged with a pivot axis 64a parallel to the longitudinal axis 62 of the cannula 5 or in one aspect with a pivot axis 64b at 90 degrees to the cannula longitudinal axis 62 as shown in FIG. 34. In one aspect, multiple lever locks are attached to the seal housing 3 and are arranged in like orientations or as mirror images as for example shown in FIG. 35. As such, in one aspect, the trocar lock 60 comprises at least one lever arm 63 pivotably movable relative to the trocar seal housing 3 and having a tab 61 extending from the at least one lever arm. The at least one lever arm is movable from a first position in which the tab engages with the aperture in the trocar seal housing 3 and the groove in the trocar cannula 5 and a second position in which the tab 61 is engaged only with the aperture in the trocar seal housing 3 or is substantially withdrawn from the groove in the trocar cannula 5.

Figure 36:
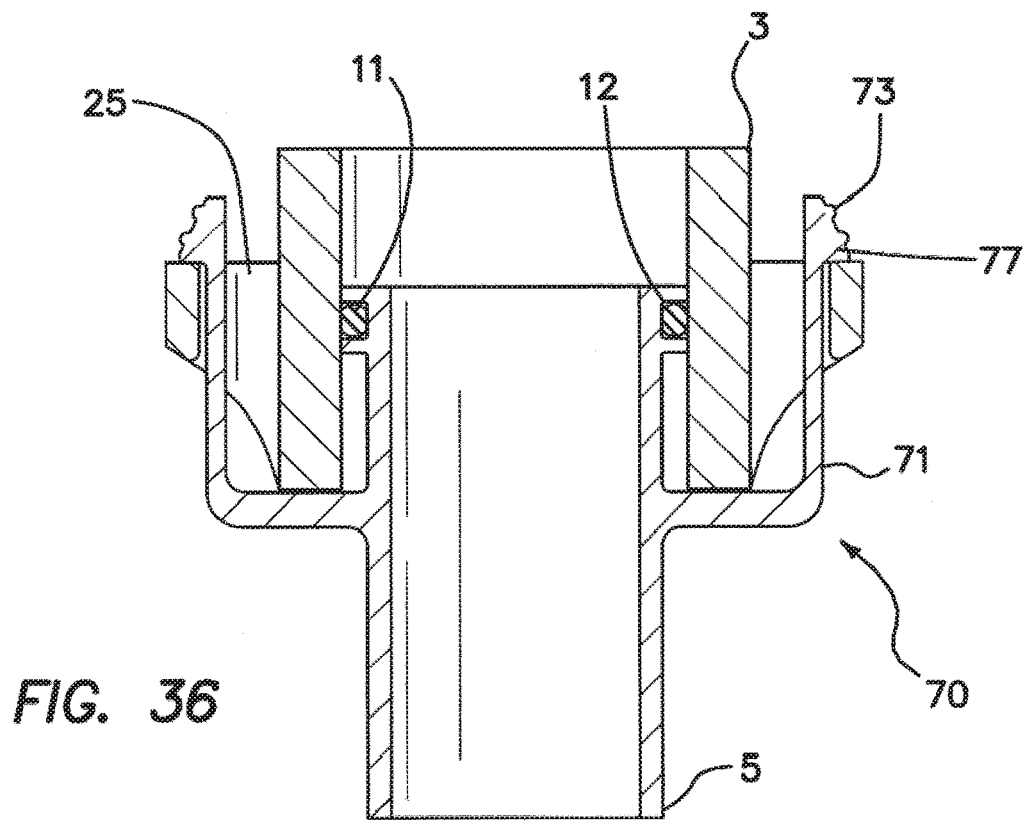
FIG. 36 is a cross-sectional side view of a surgical access port without an optical obturator and partially shown cannula and seal housing in accordance with various aspects of the present invention.

Referring to FIG. 36, the trocar cannula 5 with a seal 11, such as an o-ring or x-ring, situated in a groove 12 in the cannula 5 with a latch lock 70 is shown. In one aspect, the latch lock 70 are twin leaf spring latches 71 integral or attached to the cannula 5 with tabs or projections 77 that engage apertures or slots 25 in the seal housing 3 to secure the seal housing 3 to the cannula 5. The latches 71 are manipulated, e.g., squeezed, to withdraw the latches out of the slots 25 in the seal housing thereby allowing the seal housing 3 to be detached from the cannula 5. Grip tabs 73 extending from the latches 71 assist in manipulation, e.g., squeezing, of the latches. As such, the trocar lock 70 comprises at least one latch with a tab 77. The at least one latch is movable from a first position in which the tab 77 engages with the aperture in the aperture in the trocar seal housing 3 and the groove in the trocar cannula 5 and a second position in which the tab 77 is withdrawn from the groove in the trocar cannula 5.

Figure 37:
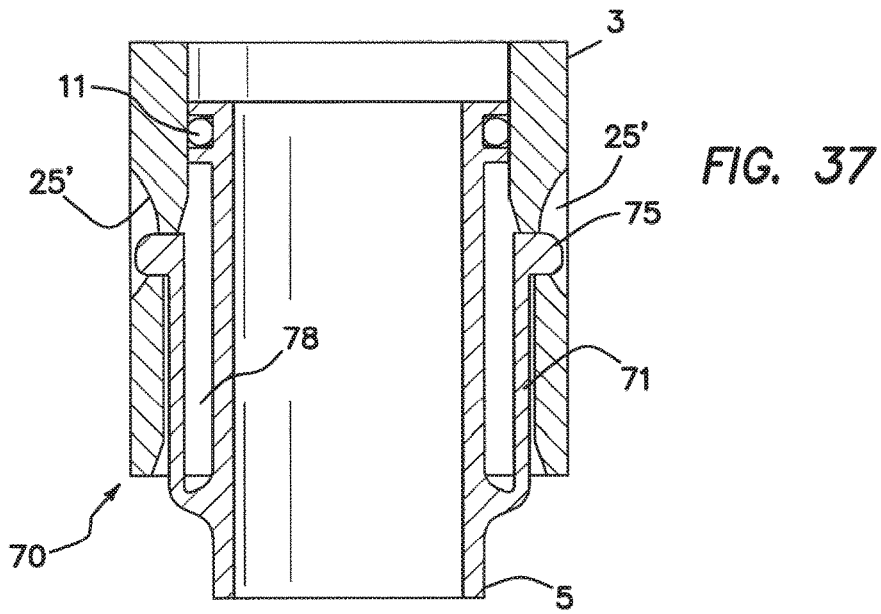
FIG. 37 is a cross-sectional side view of a surgical access port without an optical obturator and partially shown cannula and seal housing in accordance with various aspects of the present invention.

In FIG. 37, the latch arm 71 has a bulbous head 75 that engages or springs into a recessed area or curved cavity 25' of the seal housing 3. The latch lock 70 in one aspect accommodates both tensile and compressive loads between the seal housing 3 and cannula 5 and therefore serves to position the parts in relation to each other. Additional secondary ledges or stops may also be used to further enhance the locking of the seal housing 3 to the cannula 5. The radii or curve at the top and bottom of the bulbous head 75 assists the latch lock 70 in engaging and disengaging, e.g., hook and unhook, from the seal housing 3. The recess 25' in the seal housing allows the latch lock 70 to be accessed without protruding from the seal housing 3. A release button that protruded could be unintentionally squeezed during normal surgical procedures, possibly resulting in unintended detachment of the seal housing 3 from the cannula 5. The functional or manipulated area 78 of the latch lock 70 relative to the cannula 5, for example, the area allowing the latch lock to flex, in one aspect is larger than the portion of the seal housing 3 that contacts the cannula seal 12. In one aspect, the seal housing 3 inner walls are tapered, ramped or curved. As such, the cannula seal is protected as the cannula 5 passes the latch slots or aperture 25' in the seal housing 3.

Figure 38:
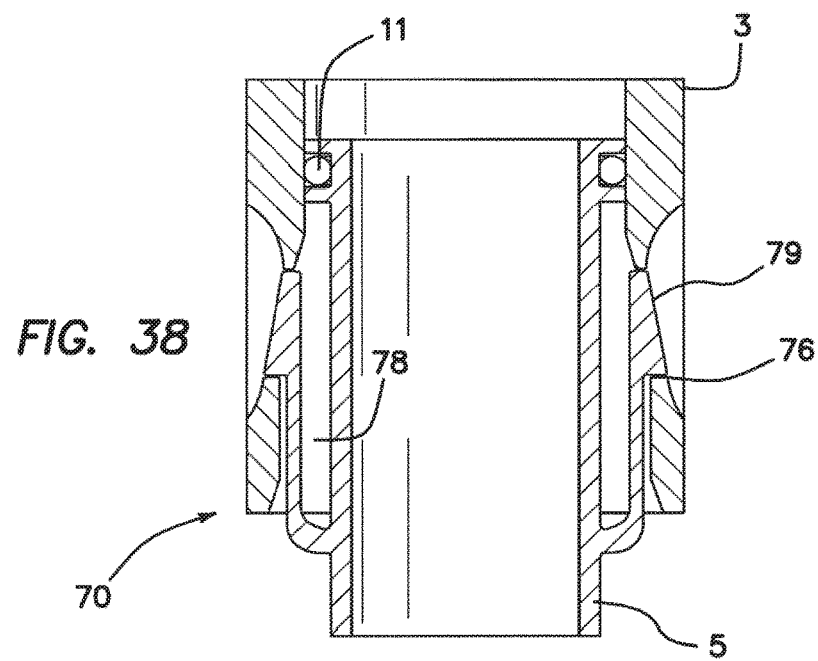
FIG. 38 is a cross-sectional side view of a surgical access port without an optical obturator and partially shown cannula and seal housing in accordance with various aspects of the present invention.

In FIG. 38, the latch lock 70 has generally triangular shaped latch heads 79. The triangular shaped latch heads 79 increase or assist in deflection of the latch lock 70 when mating the seal housing 3 and cannula 5. For example, the user would not need to hold the latch open as the parts are mated. The flat bottom 76 of the latch lock 70 ensures a positive lock while requiring a minimum of clearance to achieve the lock. An angled or overlapping latch can provide a more positive lock but may introduce more travel or play between the cannula 5 and seal housing 3. The latch lock 70 comprises of resilient or latches arms arranged external to the cannula seal lumen of the seal housing. As such, the cannula seal 11 and locking tabs or heads are generally in the same horizontal plane, resulting in a shorter seal to cannula joint. A shorter seal can be desirable for cost and ergonomic considerations. The latch lock 70 is tensile capable and as such the seal housing 3 is arranged to bottom out on the horizontal portion 76 of the latches 71.

Figure 39:
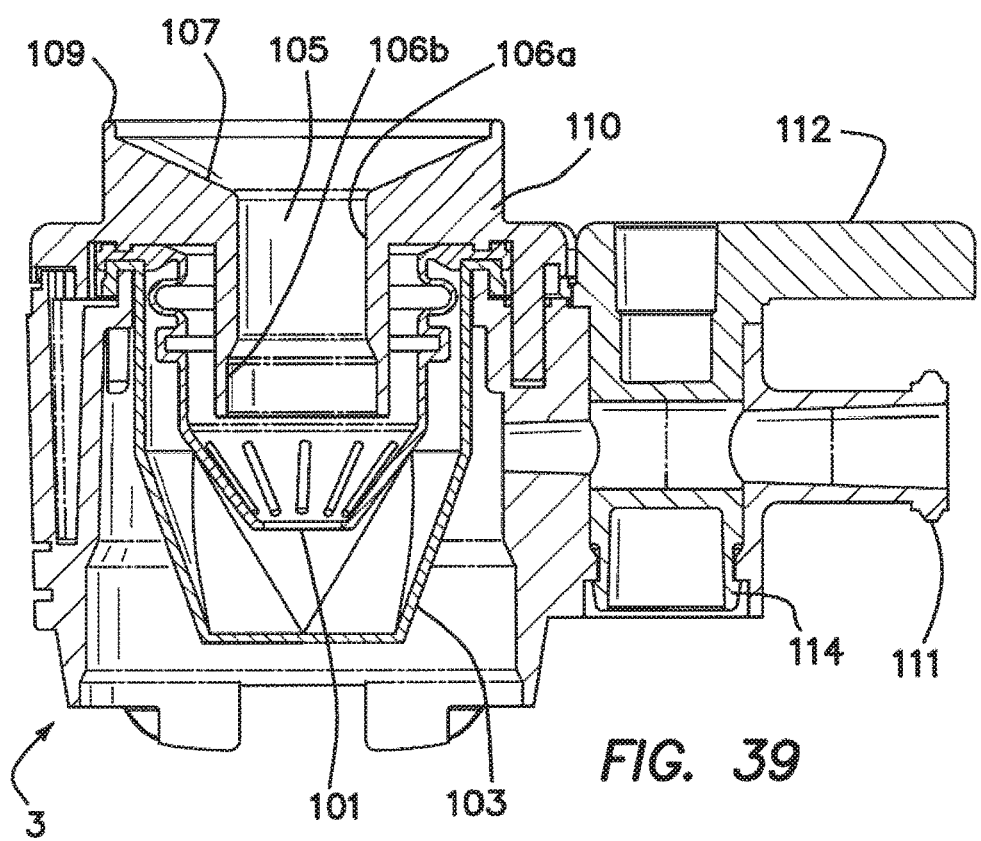
FIG. 39 is a cross-sectional side view of a trocar seal housing in accordance with various aspects of the present invention.
Figure 40:
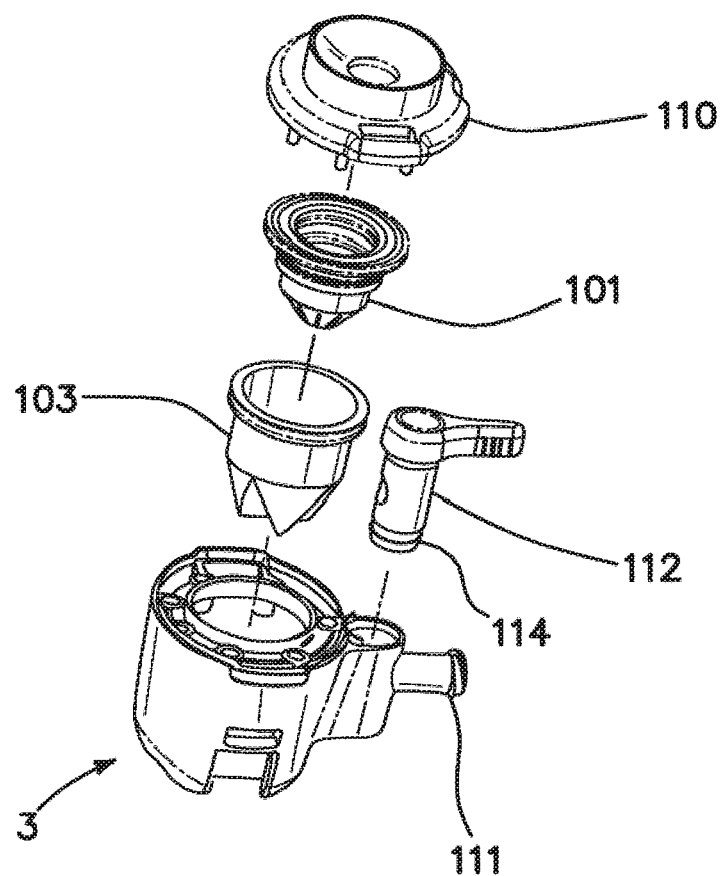
FIG. 40 is an exploded view of a trocar seal housing in accordance with various aspects of the present invention.

Referring now to FIGS. 39-40, trocar seal housing 3 holds or encloses an instrument or septum seal 101 and a zero seal 103, e.g., a duckbill seal. The septum seal 101 and the zero seal 103 are coaxially aligned with each other and a longitudinal or central axis of the trocar cannula 5 and seal housing 3. The septum seal 101 has an aperture with its center substantially in-line with the center of the trocar seal housing 3 and/or cannula 5. The septum seal 101 forms a seal to maintain pneumoperitoneum around instruments inserted through the seal's aperture while the zero seal 103 forms a seal to maintain pneumoperitoneum when no instrumentation is present in the trocar seal housing 3 and/or trocar cannula 5. The septum seal 101 in one aspect is free to swing at its distal end in response to the insertion of instrumentation or in response to the manipulation of inserted instrumentation. In one aspect, the septum seal pendulates. For example, the septum seal at its distal end moves along generally curved line or arc in response to the insertion of instrumentation or in response to the manipulation of inserted instrumentation. In one aspect, excess material, levers, bellows, convolutions or other such means pivotally connect the instrument or septum seal 101 to the trocar seal housing 3.

In one aspect, the zero seal 103 is fixed in place in contrast to the septum seal 101. In one aspect, the septum seal 101 is pivotally attached to the seal housing 3 and substantially encompassed in the fixed zero seal 103. In one aspect, the zero seal 103 is a duckbill seal fixed to the trocar seal housing 3. As such, the zero seal 103 does not swing or pendulate to a large degree, if any, relative to the septum seal 101. The zero seal 103 in combination with the septum seal 101 enables the trocar to accommodate a wide range of instrumentation diameters while minimizing the overall size of the trocar seal housing and trocar cannula.

A pendulous septum seal 101 with a zero seal attached to the pendulous septum seal can also be provided, such that pendent movement of the septum seal results in pendent movement of the zero seal. However, such a pendent trocar seal configuration can utilize a large amount of space to be accommodated within the trocar seal housing 3 and the trocar cannula 5 to enable the pendent movement of both the septum seal and the zero seal. This may result in a trocar seal with a relatively large axial length and overall diameter. The pendent septum seal 101 and a fixed zero seal 103 allows the trocar seal housing 3 and trocar cannula 5 to be sized with a reduced axial length and a reduced diameter relative to other trocar seals.

In one aspect, an instrument alignment channel 105 is juxtaposed to the septum seal 101. The alignment channel 105 in one aspect is substantially fixed and/or rigid. In one aspect, the alignment channel 105 is a long tubular channel, which extends from the proximal opening of the trocar seal to above the aperture in the septum seal 101. The alignment channel 105 serves to align or guide instrumentation during insertion and manipulation. By aligning the instrumentation and restricting the degree to which instrumentation can be manipulated, the alignment channel 105 decreases the likelihood that instrumentation can catch, tear, or otherwise disrupt the septum seal 101. Also, the alignment channel being fixed restricts the degree to which an inserted instrument can be manipulated. As such, the degree of pendulous movement utilized to accommodate instrumentation with a wide range of diameters is decreased and also the size of the trocar seal can be more compact.

The alignment channel 105 in one aspect also enables the size of the septum seal aperture to be increased. For example, the aperture in the septum seal 101 is sized to prevent cat-eye leakage during extreme lateral movement of the instrumentation. However, with a fixed instrument alignment channel 105, which is juxtaposed the septum seal 101, lateral movement of inserted instrumentation is restricted and a pendulous septum seal 101 accommodates the small amount of lateral instrumentation movement allowed by the alignment channel 105. As such, the aperture in the pendulous septum seal can be enlarged and/or tolerances relaxed. The increased diameter of the septum seal aperture results in a reduction in the drag force produced during axial movement of inserted instrumentation. A reduction in instrumentation drag force for trocar seals can aide with positioning of instrumentation relative to the operative tissue. A reduction in instrumentation drag force also decreases the likelihood that a trocar seal housing 3 and cannula 5 will be dislodged from a body wall during withdrawal of an instrument. A reduction in instrumentation drag force can also result in less fatigue for the surgeon, for example, during complex surgical procedures.

In one aspect, the alignment channel 105 has a proximal end, a distal end, and a body portion 106a extending between the proximal end and the distal end. The distal end extends into an outwardly tapered exit. In one aspect, the alignment channel 105 has an enlarged diameter at its distal end. The enlarged diameter allows for inversion of the septum seal 101 adjacent to the alignment channel 105 and prevents binding of the septum seal between the alignment channel and an instrument. For example, during withdrawal of an instrument, the septum seal 101 may invert and pull into the alignment channel 105. In one aspect, if the alignment channel 105 is not sufficiently sized, a binding or lock up effect may occur which can prevent further withdrawal of the instrument. The alignment channel 105 in one aspect has a first diameter along its body portion 106a to align instruments and to prevent excessive lateral movement of the inserted instruments. The alignment channel 105 in one aspect has a second diameter at its distal end 106b, which is larger than the first diameter. The second diameter is sized such that it can accommodate a two wall thicknesses of the septum seal and/or the largest instrument diameter that can pass through the first diameter of the alignment channel. The axial length of the enlarged diameter distal end 106b is sized such that the septum seal 101 can invert but not extend into a body portion 106a of the alignment channel with a smaller diameter portion of the alignment channel 105.

The alignment channel 105 in one aspect has an entry 107 at its proximal end that aids with insertion of instrumentation and serves to guide instrumentation into the alignment channel 105. In one aspect, the entry is generally funneled and/or tapered. As such, in one aspect, the alignment channel 105 has a proximal end and a distal end. The proximal end extends into an outwardly tapered entry. In one aspect, the tapered entry has a diameter that is larger than the diameter of the outwardly tapered exit. In one aspect, the entry has a matte finish or provides an anti-reflective or non-glare finish, coating or layer. The anti-reflective entry prevents or reduces glare and/or light from a laparoscope from being reflected back or towards the user. The entry in one aspect has a guard rail 109 at the proximal portion of the entry. The guard rail 109 in one aspect comprises a raised wall which generally encircles the top or external surface of the entry extending parallel to the longitudinal cannula axis from an end cap or wall 110 of the trocar seal housing 3. In one aspect, the trocar seal housing 3 has opening in an end cap of the trocar seal housing and an alignment channel 105 extends from the end cap 110. The septum seal 101 positioned between the alignment channel 105 and the zero seal 103. The zero seal 103 is adjacent to a proximal end of the cannula 5. In one aspect, the guard rail comprises a raised portion substantially outlining a periphery of the generally funneled entry 107. In one aspect, the guard rail integrated with or separate from the entry 107 and is a raised portion substantially outlining a periphery of an opening in a proximal end of the seal housing 3. The guard rail 109 provides a tactile hard stop to limit or prevent a surgeon from laterally sliding an instrument out of the entry 107 or alignment channel 109 during insertion of an instrument into the trocar seal housing 3.

Figure 41:
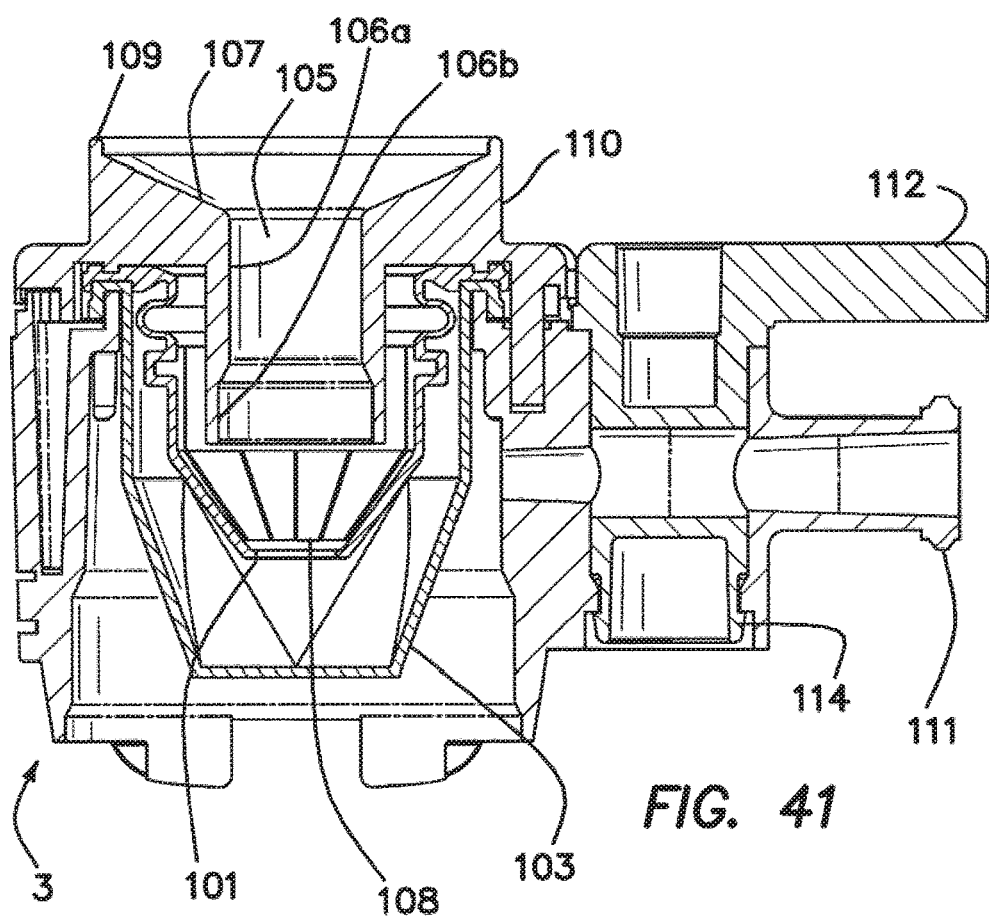
FIG. 41 is a cross-sectional side view of a trocar seal housing in accordance with various aspects of the present invention.

Referring to FIG. 41, in one aspect, the pendulous septum seal 101 is protected with a sleeve or shield 108 that is nested into the septum seal 101 and pivots with the septum seal 101. The shield prevents instruments from catching and/or tearing the septum seal. The shield 108 can also prevent the septum seal from inverting during instrument withdrawal and in one aspect is a polyethylene sleeve. The shield 108 can also reduce the instrumentation drag force and in one aspect is used in combination with the instrument alignment channel 105. The shield 108 in one aspect partially surrounds the alignment channel 105. In one aspect, the shield 108 is positioned axially between the alignment channel 105 and the septum seal 101. In one aspect, the shield 108 extends along the septum seal 101 between the alignment channel 105 and the septum seal 101.

Figure 42:
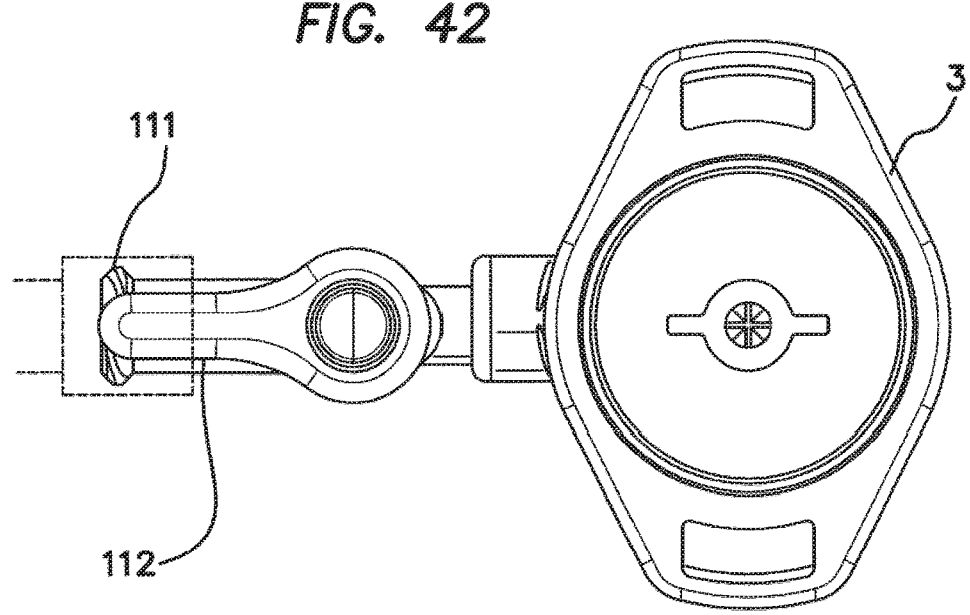
FIGS. 42-43 are plan views of a trocar seal housing in accordance with various aspects of the present invention.

In one aspect, a trocar seal housing 3 has a stopcock body 112. For example, the trocar seal housing has an integrally luer fitting inlet or molded integral luer fitting 111 and a snap fitted stopcock body 112. The stopcock body 112 in one aspect comprises a center bore and a lever. The trocar seal housing 3 with the integral luer fitting 111 is injection molded with polycarbonate. The stopcock body 112 is injection molded with polyethylene. The stopcock center bore in one aspect has a barb 114 at its distal end, which engages with a shelf on the integral luer fitting 111 to secure the stopcock body to the integral luer fitting. The trocar seal housing 3 in one aspect can have a separately assembled stopcock/luer fitting, which is then bonded or ultrasonically welded to the trocar seal housing 3 (e.g., FIG. 42). However, as shown in FIG. 41, with the trocar seal housing 3 with an integrally molded luer fitting and stopcock body, bonding or welding the stopcock can be avoided thereby eliminating at least one assembly process and one molded component thereby reducing the overall cost to produce the trocar seal. In one aspect, the integral luer fitting 111 is incorporated with and extends from the trocar seal housing 3 in a first direction for a first distance. The first direction is substantially perpendicular to a longitudinal axis of the trocar cannula 5. The stopcock 112 has a central bore extending substantially parallel to the longitudinal axis of the trocar cannula 5 and is fitted into the integral luer fitting 111. The stopcock 112 also has a lever movable by a user and extends in a second direction for a second distance. The first direction corresponds to the second direction and the first distance corresponds to the second distance.

In one aspect, the trocar seal housing 3 has an aperture with a center positioned along a first axis and is arranged to communicate gas to the trocar cannula 5. The first axis is substantially perpendicular to a longitudinal axis of the trocar cannula. The integral luer fitting 111 has an aperture with a center positioned along the first axis and is arranged to be coupled to an insufflation gas line. The stopcock 112 has a central or center bore that has a first aperture with a center and a second aperture with a center. The center bore is movable from a first position to a second position. In the first position, the center of the first aperture and the center of the second aperture are substantially aligned with the first axis. In the second position, the center of the first aperture and the center of the second aperture are out of alignment with the first axis. Examples of trocars with stopcocks or configurable with stopcocks are described in U.S. patent application Ser. No. 10/264,550, filed Oct. 4, 2002, Ser. No. 11/000,123, filed Nov. 30, 2004, and Ser. No. 10/776,387, filed Feb. 10, 2004, and U.S. Provisional Patent Application Nos. 60/529,455, filed Dec. 12, 2003, 60/492,949, filed Aug. 6, 2003, 60/312,683, filed Aug. 14, 2001, the entire disclosures of which are hereby incorporated by reference as if set in full herein.

Figure 44:
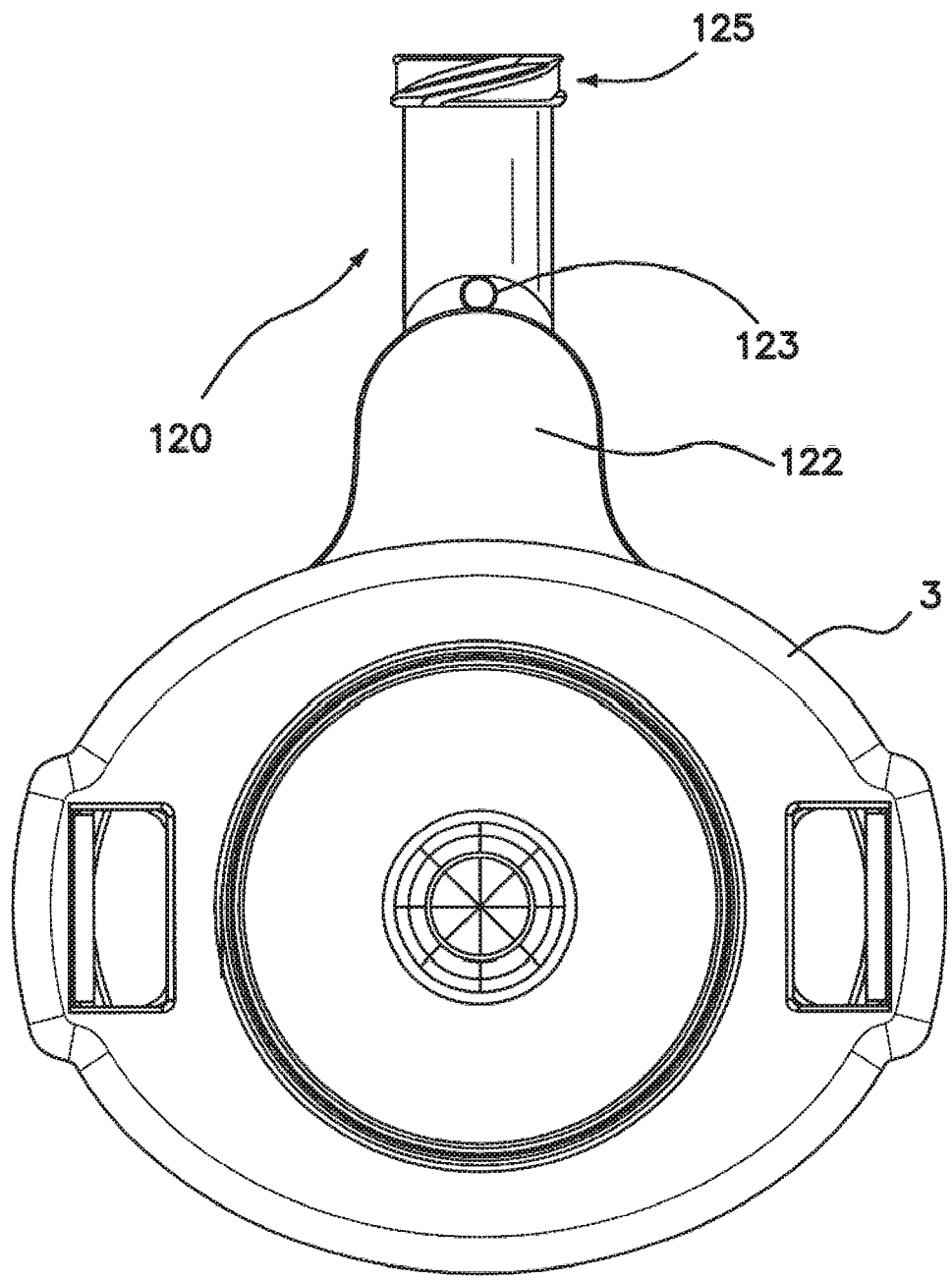
FIGS. 44-45 are plan views of a trocar seal housing in accordance with various aspects of the present invention.
Figure 45:
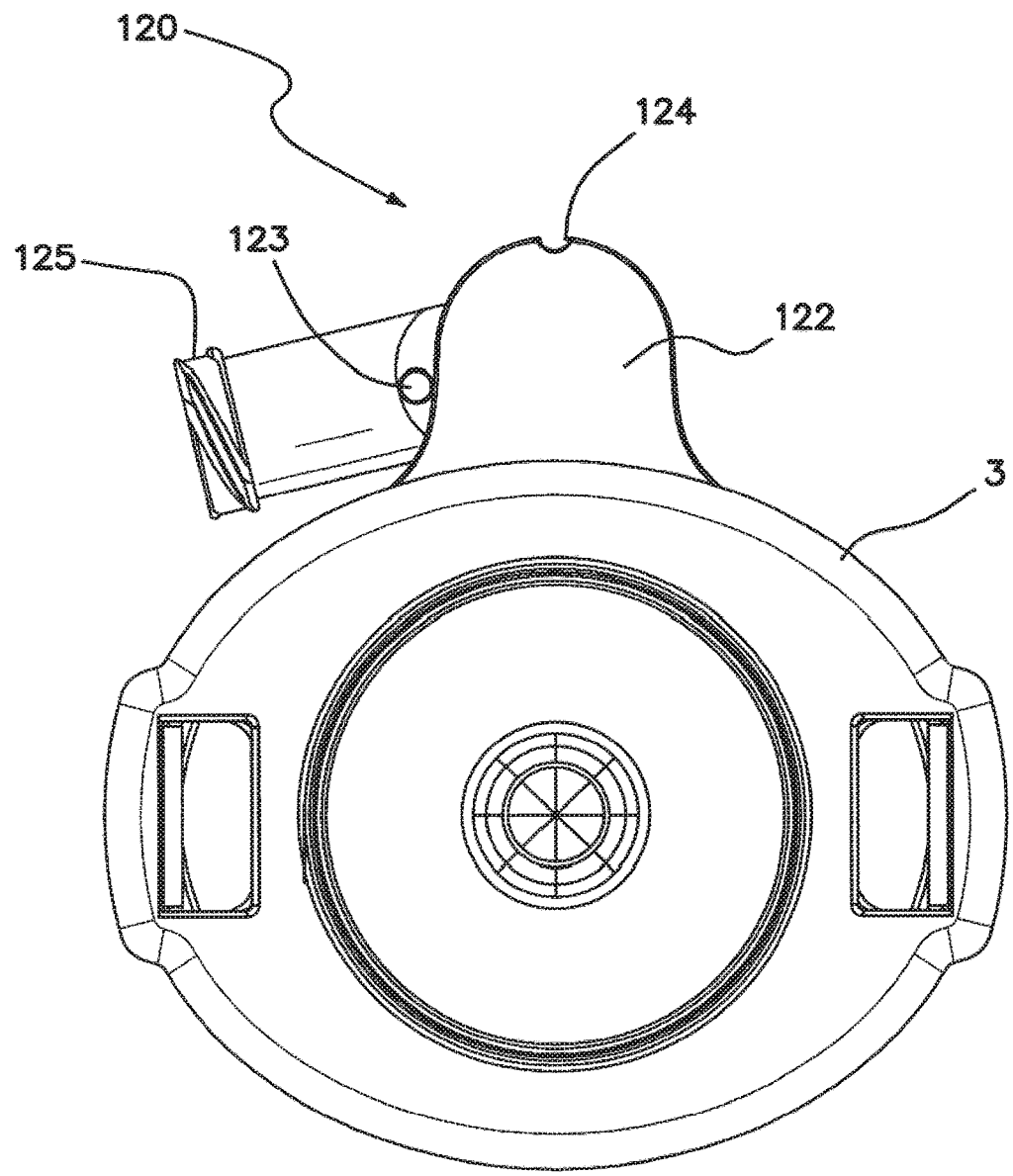
Figure 46:
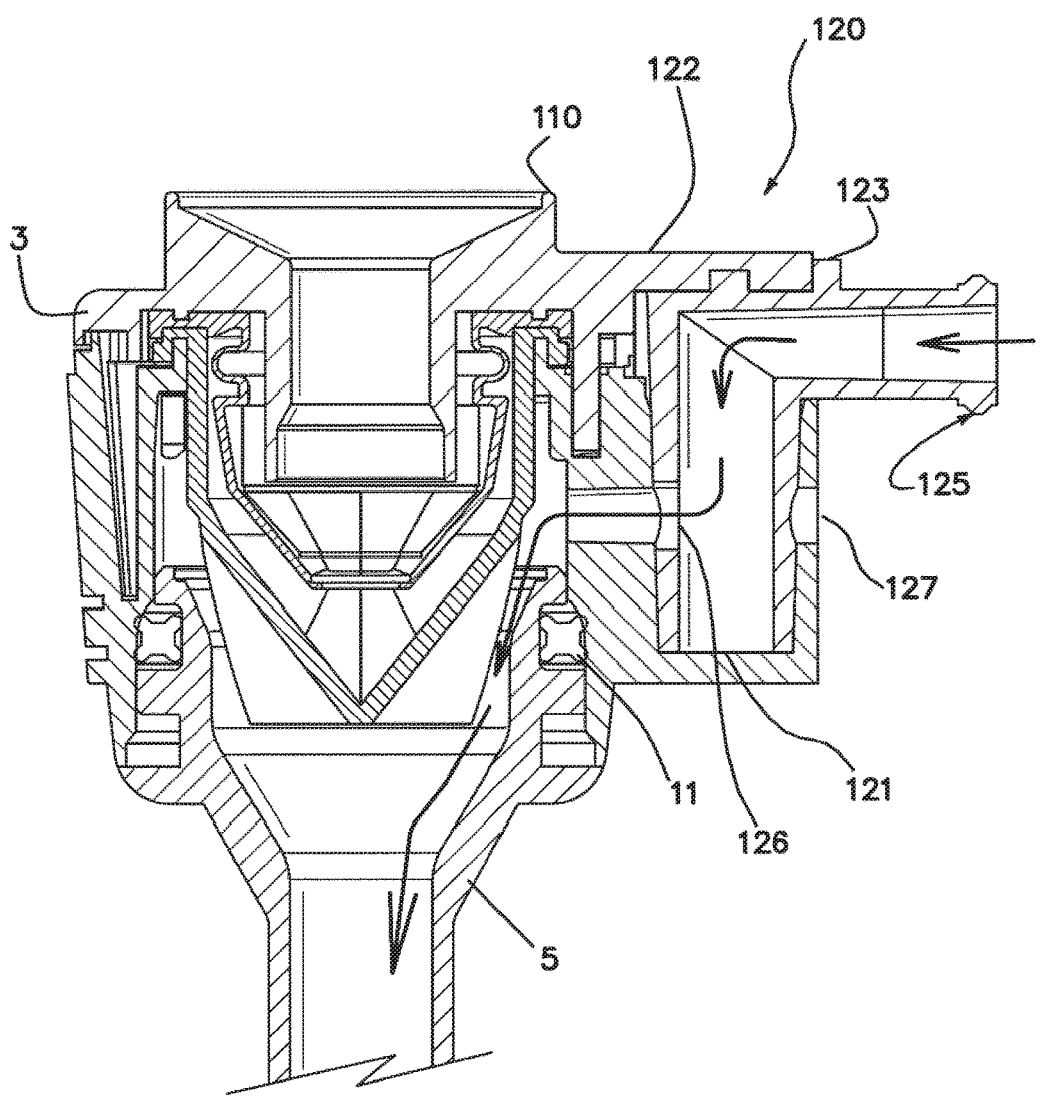
FIG. 46 is a cross-sectional side view of a trocar seal housing in accordance with various aspects of the present invention.
Figure 47:
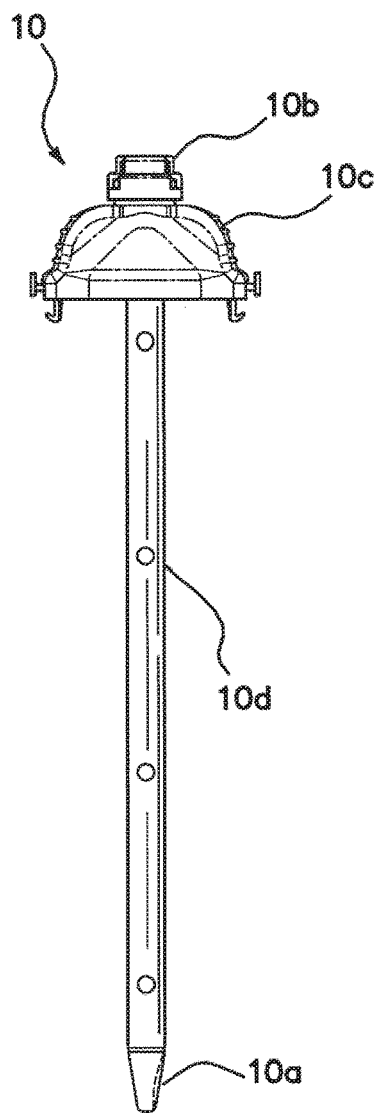
FIG. 47 is a front view of an optical obturator in accordance with various aspects of the present invention.
Figure 48:
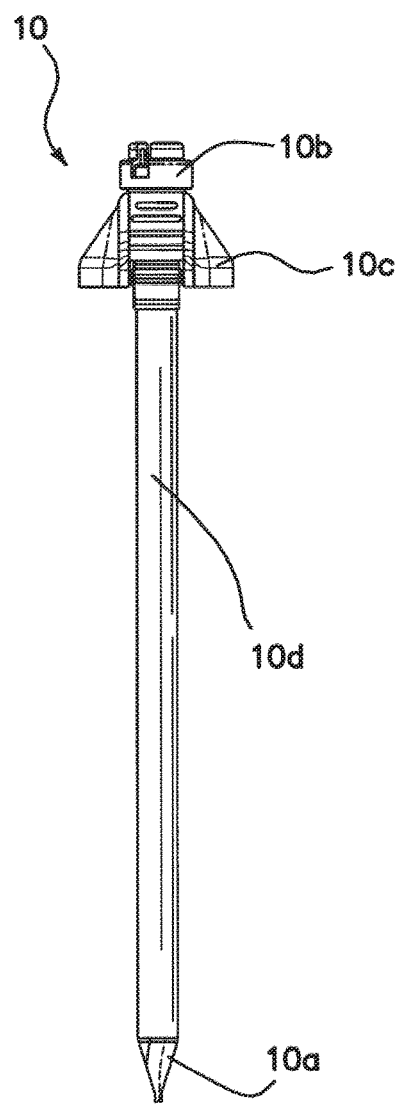
FIG. 48 is a side view of an optical obturator in accordance with various aspects of the present invention.

In one aspect, as shown for example in FIGS. 44-46, a luer fitting is integrated with a stopcock lever to form a spigot 120. With this configuration, the spigot 120 can double as a handle. As such, the spigot 120 can rotate from a high profile position to a low profile position reducing the overall profile of the trocar seal. A reduced trocar seal profile allows for greater manipulation of the trocar and enables trocars to be more closely spaced on a body wall. For example, the trocar seal housing with an integrated or combined stopcock lever and luer fitting provides a reduced "footprint" (plan view) or the area taken up by the trocar.

Figure 43:
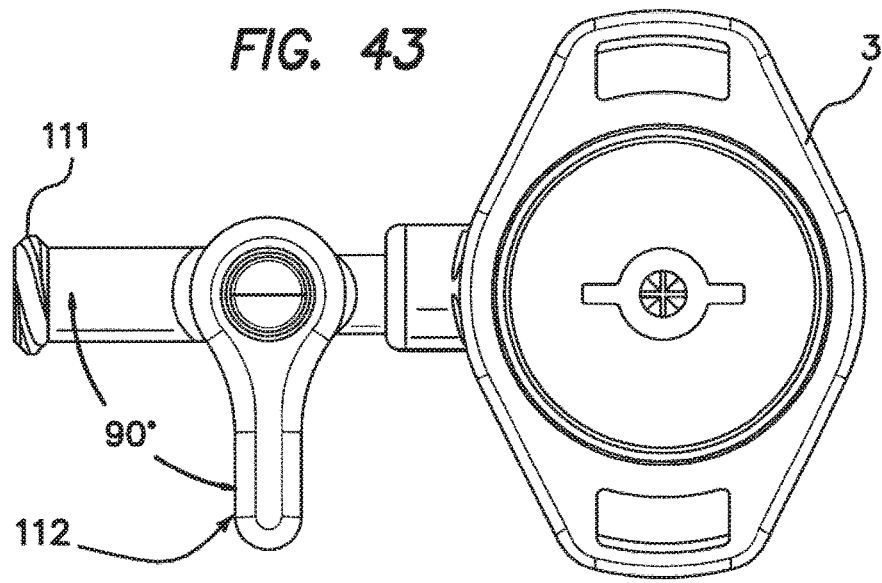

In one example, in a laparoscopic surgery three to five trocar ports can be used. Each trocar is provided with a stopcock. However, only one trocar has an open stopcock with an insufflation line attached. The stopcocks on the other the trocar are not used and are therefore closed. As shown for example in FIGS. 42-43, even though the levers are in the closed position, however, the luer inlet fitting still extends outwardly from the seal and so increases the space occupied by the trocar. In addition, the lever may only be swung 90 degrees to either side and due to geometry conditions, the lever still projects out from the trocar. As such, a closed stopcock can occupy more space than an open stopcock as two objects project outwardly from the trocar. Also, a fixed luer inlet fitting on a trocar can contact the patient's skin during extreme manipulation of the trocar, which can restrict instrument manipulation or trauma to the skin.

In one aspect, a separate stopcock/luer inlet assembly added to the trocar seal housing can result with the stopcock protruding about 1⅛" from an approximate 1" diameter seal. This changes the footprint to an approximate 1" by 2⅛" oval versus an approximate 1" circle for a non-stopcock version. In one aspect, a trocar seal housing 3 integrates the stopcock bore and luer fitting inlet into the housing. This reduces the overhang by about ¼", reducing the footprint. Also, at least one part and at least one assembly operation is eliminated. Overhang is also reduced to about ⅞" versus about 1⅛". In one aspect, a trocar seal housing 3 is provided which eliminates a fixed inlet 111 which protrudes from the trocar housing even when the valve lever is turned parallel to the body of the trocar housing (off position). In one aspect, the stopcock/inlet assembly is transformed into a combination lever and fitting, spigot 120. In the "off" position, the spigot 120 protrudes about ⅜" or so from 1" diameter housing, as the spigot can be turned past about 90 degrees to lay alongside the housing. In one aspect, the trocar cap traps the spigot in a valve bore when assembled. As such, a cap ledge in one aspect is provided above the spigot.

The spigot 120 with a reduced profile, especially when it is not in use and therefore closed, in one aspect, comprises a combined lever and luer inlet fitted to pivot to the trocar seal housing 3. In the open position, the spigot extends directly outward from the housing 3 and occupies an area similar but less than a stopcock and luer inlet fitting. When the spigot 120 is swung to the closed position, it lies closely alongside the trocar housing 3 and occupies a reduced area. In particular, no luer inlet fitting protrudes outwardly from a closed and unused fitting. In one aspect, the spigot 120 is fitted to a closed ended pivot bore 121 and is retained by a ledge 122 extending locally from the seal housing 3 or an end cap of the seal housing 3. On the other end of the spigot 120, an insufflation gas fitting end 125, e.g., a threaded end, operationally connects to an insufflation gas line. Near the closed ended pivot bore, a insufflation outlet aperture or hole 126 provides gaseous communication between the inlet or insufflation fitting end 125 and the cannula via associated apertures or channels provided in the cannula 5 and seal housing 3. The opposing end of the closed ended pivot bore has a pivot pin extending into the ledge 122 securing the spigot 120 in a pivotable relation with the seal housing 3. A hole or aperture 127 may be provided on the seal housing adjacent to spigot 120 to facilitate molding of the seal housing components.

To prevent unintended rotation, in one aspect, one or more detents 123 engaging with a corresponding cavity 124 on the end cap or wall or extended ledge 122 are provided to retain the spigot 120 in a particular positions, e.g., open and closed. In one aspect, the lever is able to rotate more than 90 degrees so as to be positioned more closely along the seal housing and therefore occupy as little space as possible. With the spigot 120 swung over alongside the seal housing, skin contact is diminished. As such, in one aspect, a pivotable spigot 120 is connected to the trocar seal housing 3. The spigot 120 has an insufflation gas fitting on one end 125 and movable between a first position to position the gas fitting extending away from and/or perpendicularly to a longitudinal axis of the trocar cannula 5 and the trocar seal housing 3 and a second position to position the gas fitting extending close to and/or positioned substantially near the seal housing 3.

Figures 49A, 49B:
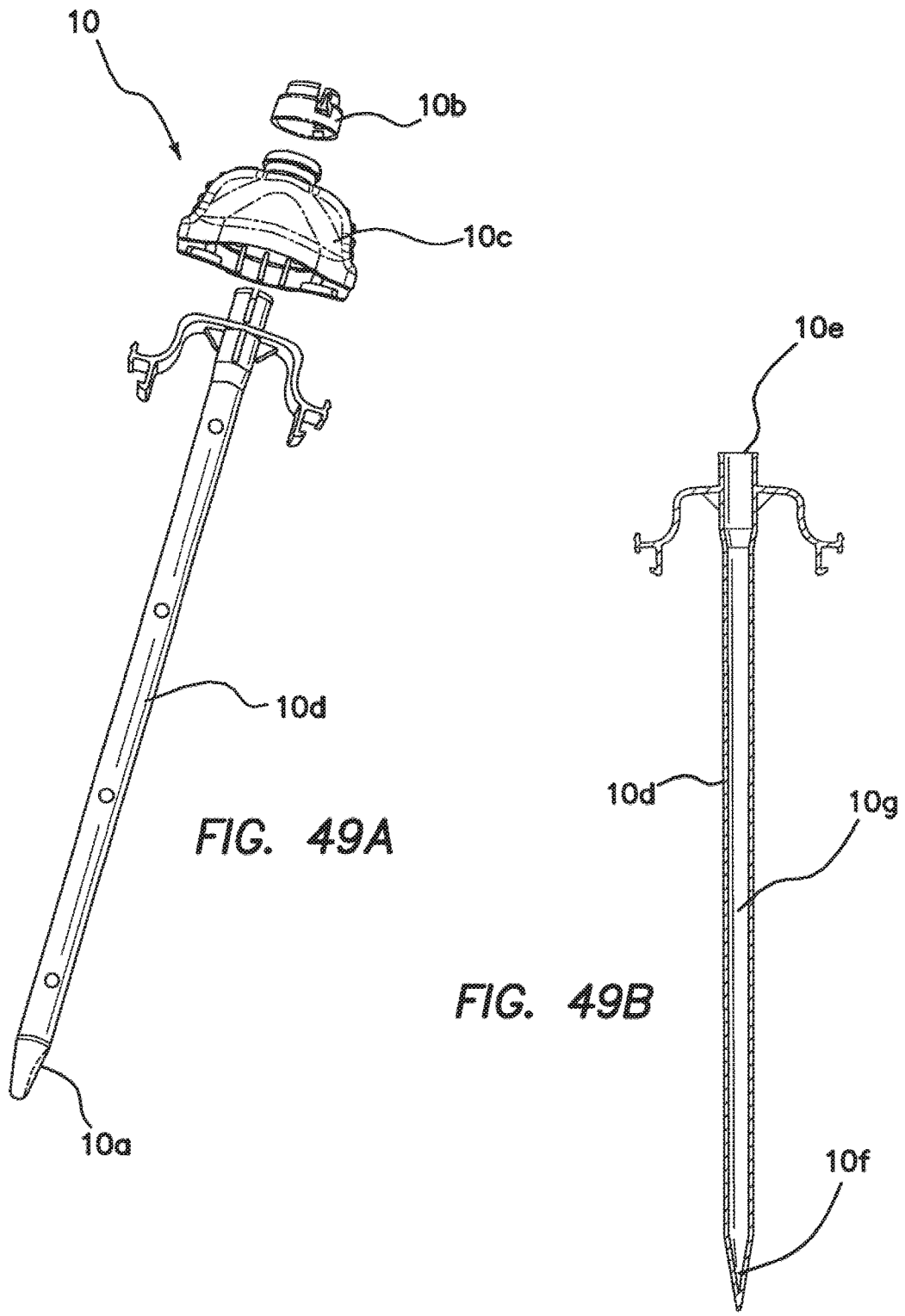
FIG. 49A is an exploded view of an optical obturator in accordance with various aspects of the present invention.
FIG. 49B is a longitudinal cross section of the shaft of the obturator illustrated in FIG. 49A.
Figure 50:
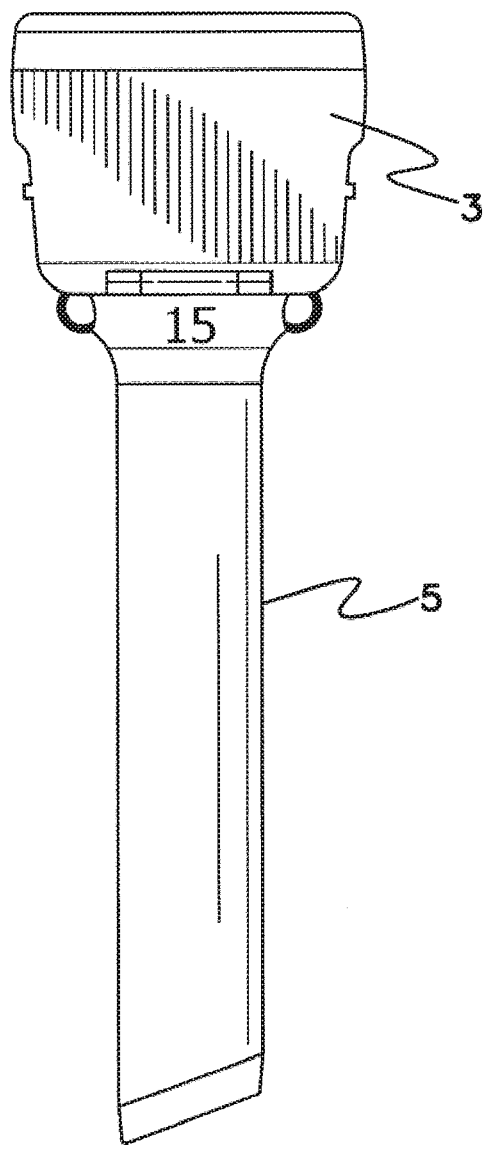
FIG. 50 is a front view of a surgical access port without an optical obturator in accordance with various aspects of the present invention.
Figure 53:
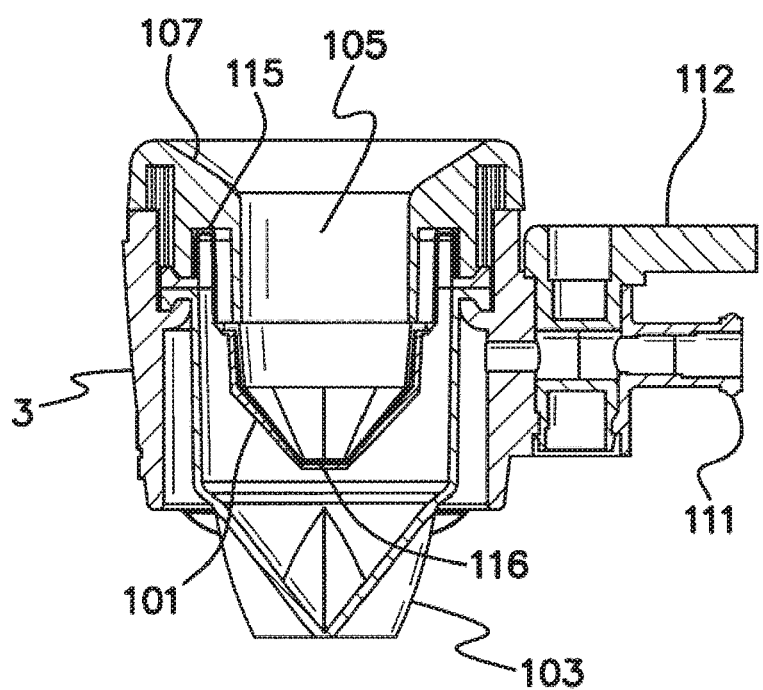
FIG. 53 is a cross-sectional side view of a trocar seal housing in accordance with various aspects of the present invention.
Figure 54:
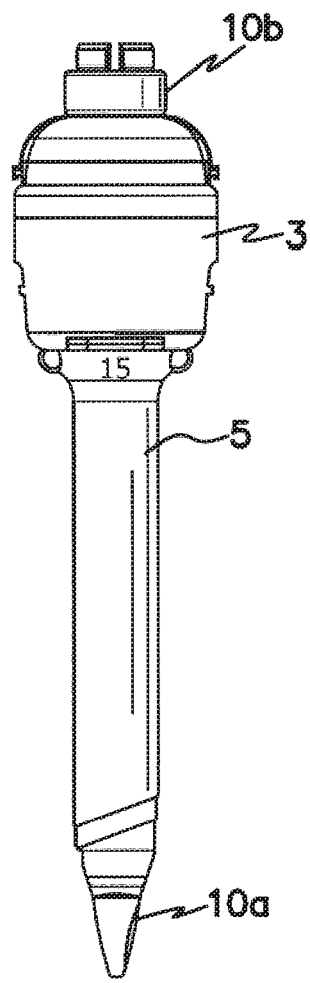
FIG. 54 is a front view of a surgical access port in accordance with various aspects of the present invention.
Figure 55:
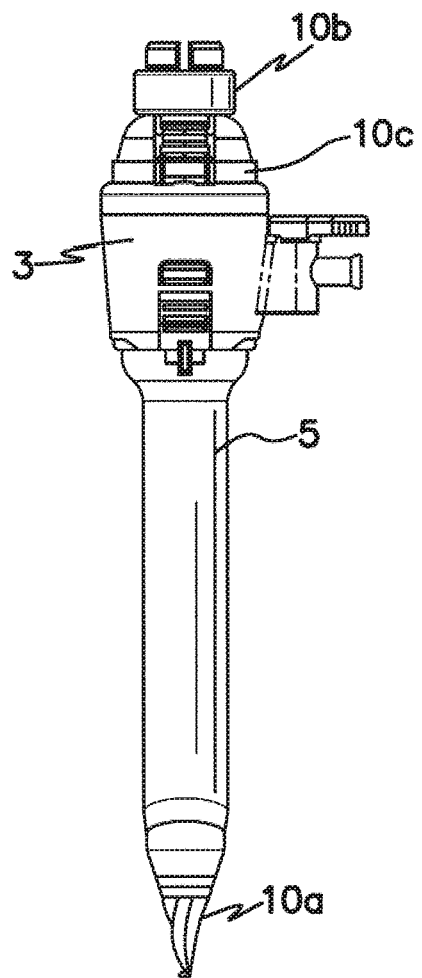
FIG. 55 is a side view of a surgical access port in accordance with various aspects of the present invention.

Referring now to FIGS. 47-49B, an optical obturator 10 in one aspect is configured to separate muscle fibers and tissue during placement of the trocar across a body wall. The trocar seal housing 3 and cannula 5 with the inserted obturator 10 is alternately twisted back and forth as a small axial force is applied to traverse a body wall. The cross sectional profile of the obturator tip 10a is configured such that its width is greater than its length. Rotation of the obturator 10 causes muscle fibers and tissue to separate along natural planes. The optical obturator 10 in one aspect is formed of a transparent high-flow polycarbonate material to enable visualization of tissue fibers during traversal across a body wall. Visualization can be achieved by inserting a laparoscope with an attached camera into the inside diameter of the obturator 10. The tissue is viewed through the tip 10a of the obturator as the trocar traverses a body wall. In one aspect, a laparoscope is allowed to be positioned within a portion of the obturator tip 10a enhancing visualization. Referring to FIG. 49B, in one aspect, the obturator 10 has a longitudinally extending lumen 10g from a proximal open end 10e to a distal closed end 10f. The lumen 10g is sized and arranged to receive a laparoscope and the obturator 10 is sized to be slidably movable in the lumen of the trocar cannula 5.

In one aspect, the tip portion of the obturator is molded. The injection mold for the obturator is configured such that the distal tip of the obturator, which in one aspect is the portion that contacts and separates body wall tissue, does not include any mold parting lines and/or injection molding gates. The tip 10a therefore is smooth with a high degree of clarity and is free of any artifacts produced as a result of injection molding such as parting line flash, parting line mismatch, gate recesses, gate remnants, and gate blush. An optical obturator 10 with these artifacts from injection molding may catch body wall tissue such as the peritoneum. The image produced through the optical obturator is also enhanced, as the tip of the obturator does not include parting lines, a gate remnant, a gate recess, or gate blush, all of which may reduce the optical clarity of an optical obturator.

Referring now to FIGS. 50-55, the access port comprises a seal housing 3 releasably attached to a cannula 5. The seal housing 5 holds a pendulous septum seal 101, which has a convolution 115 of excess material at its proximal end. The convolution 115 enables the septum seal 101 to pivot in response to the insertion of an instrument such that the septum seal can align itself with the inserted instrument. The convolution 115 also allows the septum seal 101 to pivot during off-axis movement of an inserted instrument such that a seal is maintained between the septum seal 101 and the inserted instrument. The septum seal 101 is designed with the convolution 115 such that there are no undercuts on the part. By providing a part with no undercuts, the septum seal 101 can be transfer molded with relatively simple multi-cavity mold tooling. In one aspect, convolutions 115, excess material, levers, bellows, or other such means pivotally connect the instrument or septum seal 101 to the trocar seal housing 3.

In one aspect, the trocar seal comprises a septum shield 116 adjacent to the septum seal 101. The septum shield is arranged such that it abuts the distal portion of the alignment channel 105. In one aspect, the septum shield 116 has a proximal flat portion in contact with the alignment channel 105. This minimizes the axial movement of the septum shield 116 during withdrawal of an inserted instrument. The septum seal in one aspect comprises an annular rib positioned between the alignment channel 105 and the septum shield 116. The annular rib for example abuts the distal portion of the alignment channel 105 and extends perpendicular to the longitudinal axis of the trocar cannula. The annular rib in one aspect holds the shield in place in the septum shield. In one aspect, the septum shield 116 partially surrounds the alignment channel. In one aspect, the septum shield 116 is positioned axially between the alignment channel and the septum seal 101. In one aspect, the septum shield 116 extends along the septum seal 101 between the alignment channel 105 and the septum seal 101.

The septum seal 101 in one aspect is configured with varying wall thicknesses in the convolution portion 115 of the seal 101 to minimize axial movement of the septum seal 101 during the insertion or distal advancement of an instrument. For example, the outer wall of the convolution 115 can be configured with a thicker wall than the inner wall of the convolution 115. This would allow the septum seal 101 to pivot yet would inhibit the axial movement of the septum seal 101 in the distal direction.

The septum seal 101 in one aspect has a plurality of radially spaced vertical ribs on an outside wall or surface of the convolution 115. The radially spaced ribs allow the septum seal 101 to pivot yet inhibits the axial movement of the septum seal 101 in the distal direction. The most proximal portion of the convolution 115 in one aspect is arranged to have a thinner wall thickness than either the outer wall or the inner wall of the convolution 115. This enables the septum seal 101 to easily pivot yet inhibits the axial movement of the septum seal 101 in the distal direction. The convolution 115 in one aspect comprises a plurality of radially spaced ribs, which would span the gap between the outer wall of the convolution and the inner wall of the convolution. The ribs would be thin enough to allow the septum seal 101 to pivot yet would inhibit the axial movement of the septum seal 101 in the distal direction. By minimizing or inhibiting the axial movement of the septum seal 101 in the distal direction this allows or facilitates the trocar seal to be arranged more compactly with a reduced overall height.

In various aspects, the trocar seal housing 3 has opening in an end cap 110 of the trocar seal housing and an alignment channel 105 extends from the end cap 110. The septum seal 101 is positioned between the alignment channel 105 and the zero seal 103. The zero seal 103 is also adjacent to a proximal end of the cannula 5. The access port in one aspect comprises a seal housing 3, which is releasably attached to the cannula 5 via for example cantilever snap arms 7 to enable removal of tissue specimens and to enable rapid desufflation of a body cavity. Suture ties loops or eyes 8 in one aspect are generally circular apertures extending from opposing sides of the cannula 5. The access port in one aspect accommodates a blunt optical obturator arranged to be used in conjunction with an inserted laparoscope to allow visualization of tissue during traversal across a body wall. The optical obturator 10 in one aspect has a laparoscope lock 10b arranged to allow rotation of the laparoscope within the obturator while preventing axial movement of the laparoscope within the obturator.

The trocar seal housing 3 and cannula 5 in one aspect comprises multiple components. The trocar cannula 5 is an injection molded polycarbonate. Attached to the trocar cannula 5 is an EPDM (Ethylene Propylene Diene Monomer) O-ring seal. In one aspect, the cannula seal 11 is overmolded seal comprising of silicone, KRATON, styrene-ethylene/butylene-styrene, copolyester, copolyamide, thermoplastic rubber, thermoplastic vulcanite, C-FLEX, or a thermoplastic elastomeric material molded into a polycarbonate trocar cannula. The trocar seal housing 3 has an injection molded polycarbonate housing, an injection molded polycarbonate cap, an injection molded polycarbonate shield, a compression molded polyisoprene septum seal 101, a compression molded polyisoprene duckbill valve 103, and an injection molded polyethylene stopcock body 112. To assemble the trocar seal, the stopcock lever is snap fitted into the integral luer fitting 111 of the housing 3. The duckbill valve 103 is seated into the housing 3. The septum seal 101 is nested into the duckbill valve 103. The cap is press fitted onto the housing 3. The assembled trocar seal housing 3 is snap fitted onto the trocar cannula 5.

The optical obturator 10 in one aspect comprises three components; an injection molded polycarbonate obturator shaft 10d, an injection molded polycarbonate knob 10c, and an injection molded polycarbonate scope lock 10b. The scope lock retains the axial position of an inserted laparoscope. Assembly of the obturator in one aspect comprises snap fitting the knob onto the obturator shaft. The scope lock snap fits onto the knob.

In one aspect, the trocar cannula 5 and o-ring are formed of reusable materials enabling autoclave sterilization and re-use of the cannula and o-ring. In one aspect, the optical obturator shaft is formed of an extruded plastic tube or a metal tube. The tip portion 10a is bonded to the tube or overmolded onto the tube. In one aspect, the zero seal 103 is a double duckbill valve, a single duckbill, a gel seal, an overlapping flap seal, and/or a slit seal. In one aspect, the septum seal 101 and the zero seal 103 may be coated with parylene, silicone grease, mineral oil, glycerin, Teflon, silicone oil, or a combination thereof to reduce instrument drag forces. The septum seal 101 and zero seal 103 in one aspect is chlorinated or plasma etched to reduce instrument drag forces.

In various aspects, the trocar lock is arranged to resist axial forces directed to separate the trocar cannula from the trocar seal housing. In one example, a trocar lock has a tab extending from the trocar lock and is movable through an aperture in the trocar seal housing to a groove in the trocar cannula. In one example, a trocar lock extends from the trocar cannula and has a tab that is engagable with a slot in the trocar seal housing. In various aspects, a trocar seal housing is provided which easily attaches to and easily detaches from a trocar cannula, has a pendulous septum seal with a zero seal, a fixed instrument alignment channel, a shield protecting the septum seal, an instrument alignment channel with an enlarged space to allow for inversion of the septum seal, an optical obturator with a tip that has a high degree of optical clarity and/or with an outer surface that is smooth, or any combination thereof. Examples of pendulous seals are described in U.S. patent application Ser. No. 10/264,550, filed Oct. 4, 2002, the entire disclosure of which is hereby incorporated by reference as if set in full herein. Examples of shielded septum seals are described in U.S. patent application Ser. No. 11/000,123, filed Nov. 30, 2004, and U.S. Provisional Patent Application No. 60/529,455, filed Dec. 12, 2003, the entire disclosures of which are hereby incorporated by reference as if set in full herein. Examples of optical obturators are described in U.S. patent application Ser. No. 10/956,167, filed Oct. 1, 2004, and U.S. Provisional Patent Application No. 60/508,390, filed Oct. 3, 2003, the entire disclosures of which are hereby incorporated by reference as if set in full herein.

Although the present invention has been described in certain specific aspects, many additional modifications and variations would be apparent to those skilled in the art. It is therefore to be understood that the present invention may be practiced otherwise than specifically described, including various changes in the size, shape and materials, without departing from the scope and spirit of the present invention. Thus, embodiments of the present invention should be considered in all respects as illustrative and not restrictive.

The invention claimed is:

1. A surgical access port to access a body cavity and sealingly engage a surgical instrument inserted therethrough, the surgical access port comprising:
   a trocar seal housing comprising:
      an instrument seal configured to form a seal around the surgical instrument inserted through the surgical access port;
      a zero seal configured to form a seal when no surgical instrument is present in the surgical access port;
      a first slot and a second slot on opposing sides of the trocar seal housing;
   a trocar cannula comprising a first cantilever arm and a second cantilever arm extending proximally therefrom;
   a trocar lock releasably attaching the trocar seal housing to the trocar cannula, the trocar lock defined by the first cantilever arm and the second cantilever arm operationally engageable with the first slot and the second slot.

2. The surgical access port of claim 1, wherein the first cantilever arm and the second cantilever arm each comprise a proximal end and a hook positioned at the proximal end.

3. The surgical access port of claim 2, wherein the first slot and the second slot each comprise a ledge engageable by the hooks of the first and second cantilever arms to maintain an axial position of the trocar seal housing relative to the trocar cannula.

4. The surgical access port of claim 3, wherein the first cantilever arm and the second cantilever arm each comprise a resilient arm and wherein the first cantilever arm and the second cantilever arm each comprise a finger tab movable radially inward to disengage the hooks of the first cantilever arm and the second cantilever arm from the ledges of the first slot and the second slot.

5. The surgical access port of claim 1, wherein the trocar cannula comprises a sealing ring positioned to sealingly engage the trocar seal housing with the trocar seal housing attached to the trocar cannula.

6. The surgical access port of claim 5, wherein the sealing ring comprises an o-ring.

7. The surgical access port of claim 5, wherein the trocar cannula comprises an annular groove in which the sealing ring is received.

8. A surgical access port to access a body cavity and sealingly engage a surgical instrument inserted therethrough, the surgical access port comprising:
 a trocar seal housing having a proximal end and a distal end and a longitudinal axis extending from the proximal end to the distal end, the trocar seal housing comprising:
  an end cap disposed at the proximal end of the trocar seal housing;
  an alignment channel extending distally from the end cap;
  a pendulous septum seal positioned distally of the alignment channel;
  a zero seal coaxially aligned with the septum seal and positioned distally of the septum seal; and
  an integral luer fitting in fluid communication with the distal end of the trocar seal housing, and further comprising a shield nested into the septum seal and pivotable with the septum seal.

9. The surgical access port of claim 8, wherein the end cap comprises a generally funneled entry at the proximal end of the trocar seal housing.

10. The surgical access port of claim 9, wherein the end cap further comprises a guard rail comprising a raised portion substantially outlining a periphery of the funneled entry.

11. The surgical access port of claim 8, further comprising a stopcock body fit into the luer fitting.

12. The surgical access port of claim 11, wherein the stopcock body comprises a barb configured to snap fit with the luer fitting.

13. A surgical access port to access a body cavity and sealingly engage a surgical instrument inserted therethrough, the surgical access port comprising:
 a trocar seal housing configured to form a seal around the surgical instrument inserted through the surgical access port, the trocar seal housing comprising:
  a first slot on a side of the trocar seal housing; and
  a second slot on an opposing side of the trocar seal housing;
 a trocar cannula comprising:
  a sealing ring positioned to engage the trocar seal housing;
  a first cantilever arm extending proximally from the trocar cannula; and
  a second cantilever arm extending proximally from the trocar cannula; and
 a trocar lock releasably attaching the trocar seal housing to the trocar cannula, the trocar lock defined by the first cantilever arm and the second cantilever arm operationally engageable with the first slot and the second slot such that the first cantilever arm and the second cantilever arm are recessed from an outer surface of the trocar seal housing with the first cantilever arm and the second cantilever arm engaged with the first slot and the second slot.

14. The surgical access port of claim 13, wherein the first cantilever arm and the second cantilever arm each comprise a generally triangular latch head.

15. The surgical access port of claim 14, wherein the sealing ring and the triangular latch head of each of the first and the second cantilever arms are positioned in a generally horizontal plane.

16. The surgical access port of claim 14, wherein the generally triangular latch head of each of the first and the second cantilever arms comprises a flat bottom surface.

17. A surgical access port to access a body cavity and sealingly engage a surgical instrument inserted therethrough, the surgical access port comprising:
 a trocar seal housing having a proximal end and a distal end and a longitudinal axis extending from the proximal end to the distal end, the trocar seal housing comprising:
  an end cap disposed at the proximal end of the trocar seal housing;
  an alignment channel extending distally from the end cap;
  a pendulous septum seal positioned distally of the alignment channel;
  a zero seal coaxially aligned with the septum seal and positioned distally of the septum seal; and
  an integral luer fitting in fluid communication with the distal end of the trocar seal housing, and
 wherein the alignment channel comprises an elongate tubular channel comprising a body portion having a first diameter and a distal end having an enlarged diameter relative to the first diameter.

18. The surgical access port of claim 17, wherein the alignment channel further comprises a proximal end proximal of the body portion, the proximal end of the alignment channel comprising a funneled entry.

* * * * *